US012383173B2

(12) United States Patent
Bohm et al.

(10) Patent No.: US 12,383,173 B2
(45) Date of Patent: Aug. 12, 2025

(54) ANALYTE SENSOR WITH IMPEDANCE DETERMINATION

(71) Applicant: DexCom, Inc., San Diego, CA (US)

(72) Inventors: Sebastian Bohm, San Diego, CA (US); Anna Claire Harley-Trochimczyk, San Diego, CA (US); Daiting Rong, San Diego, CA (US); Rui Ma, San Diego, CA (US); Wenjie Lan, San Diego, CA (US); Minglian Shi, San Diego, CA (US); Disha B. Sheth, Oceanside, CA (US); Nicholas Kalfas, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 611 days.

(21) Appl. No.: 16/728,676

(22) Filed: Dec. 27, 2019

(65) Prior Publication Data
US 2020/0205701 A1    Jul. 2, 2020

Related U.S. Application Data

(60) Provisional application No. 62/786,166, filed on Dec. 28, 2018, provisional application No. 62/786,127, (Continued)

(51) Int. Cl.
*A61B 5/1495*    (2006.01)
*A61B 5/145*    (2006.01)
(Continued)

(52) U.S. Cl.
CPC ........ *A61B 5/1495* (2013.01); *A61B 5/14532* (2013.01); *A61B 5/1486* (2013.01);
(Continued)

(58) Field of Classification Search
CPC ... C12Q 1/001–006; G01N 27/02–021; G01N 27/026–028; G01N 27/045–048;
(Continued)

(56) References Cited

U.S. PATENT DOCUMENTS 5,800,420 A * 9/1998 Gross ................ A61M 5/14244
600/347
6,001,067 A 12/1999 Shults et al.
(Continued)

FOREIGN PATENT DOCUMENTS

GB    1505343 A    3/1978
JP    2000171431 A    6/2000
(Continued)

OTHER PUBLICATIONS

International Search Report and Written Opinion for Application No. PCT/US2019/068713 mailed on Apr. 16, 2020, 11 pages.

*Primary Examiner* — Tse W Chen
*Assistant Examiner* — Alice Ling Zou
(74) *Attorney, Agent, or Firm* — Schwegman, Lundberg & Woessner, P.A.

(57)    ABSTRACT

Various examples described herein are directed to systems and methods for determining an analyte concentration using an analyte sensor. A method may comprise disconnecting an analyte sensor from a measurement circuit and reconnecting the analyte sensor to the measurement circuit after an accumulation period. The method may comprise receiving a signal from the analyte sensor. The signal may be indicative of an amount of charge accumulated on the analyte sensor during the accumulation period. The method may also comprise determining an estimated analyte concentration level based on the received signal.

32 Claims, 26 Drawing Sheets

Related U.S. Application Data filed on Dec. 28, 2018, provisional application No. 62/786,116, filed on Dec. 28, 2018, provisional application No. 62/786,228, filed on Dec. 28, 2018, provisional application No. 62/786,208, filed on Dec. 28, 2018.

(51) Int. Cl.
| | |
|---|---|
| *A61B 5/1486* | (2006.01) |
| *G01N 27/22* | (2006.01) |
| *G01N 27/24* | (2006.01) |
| *G01N 33/487* | (2006.01) |
| *G01N 27/02* | (2006.01) |

(52) U.S. Cl.
CPC ....... *A61B 5/14865* (2013.01); *G01N 27/221* (2013.01); *G01N 27/24* (2013.01); *G01N 33/48707* (2013.01); *A61B 2560/0223* (2013.01); *A61B 2560/0252* (2013.01); *A61B 2560/0276* (2013.01); *G01N 27/026* (2013.01)

(58) Field of Classification Search
CPC ......... G01N 27/12–121; G01N 27/221; G01N 27/223; G01N 27/228; G01N 27/24; G01N 27/26–27; G01N 27/3271–3272; G01N 27/3274; G01N 27/3273; G01N 27/3276–3277; G01N 27/40; G01N 27/4163; G01N 33/5438; G01N 33/557; G01N 33/66; A61B 5/14503; A61B 5/1451; A61B 5/14532; A61B 5/14546; A61B 5/1486–14865; A61B 5/1468–14735; A61B 5/1495; A61B 5/7203; A61B 5/7225; A61B 2560/02; A61B 2560/0223; A61B 2560/0242–0252; A61B 2560/0276; A61B 5/7221; A61B 2560/0266; A61B 5/053

See application file for complete search history.

(56) References Cited

U.S. PATENT DOCUMENTS

| | | |
|---|---|---|
| 6,424,847 B1 | 7/2002 | Mastrototaro et al. |
| 6,477,395 B2 | 11/2002 | Schulman et al. |
| 6,484,046 B1 | 11/2002 | Say et al. |
| 6,512,939 B1 | 1/2003 | Colvin et al. |
| 6,565,509 B1 | 5/2003 | Say et al. |
| 6,579,690 B1 | 6/2003 | Bonnecaze et al. |
| 7,494,465 B2 | 2/2009 | Brister et al. |
| 8,372,266 B2 | 2/2013 | Biswas et al. |
| 8,682,408 B2 | 3/2014 | Boock et al. |
| 8,834,707 B2 | 9/2014 | Milam et al. |
| 9,044,199 B2 | 6/2015 | Brister et al. |
| 9,481,917 B2 | 11/2016 | Bochiechio et al. |
| 9,808,190 B2 | 11/2017 | Bohm et al. |
| 2002/0098119 A1 | 7/2002 | Goodman |
| 2003/0191376 A1 | 10/2003 | Samuels et al. |
| 2005/0027463 A1 | 2/2005 | Goode, Jr. et al. |
| 2005/0043598 A1 | 2/2005 | Goode, Jr. et al. |
| 2006/0020187 A1 | 1/2006 | Brister et al. |
| 2007/0027385 A1 | 2/2007 | Brister et al. |
| 2007/0128681 A1 | 6/2007 | Barman et al. |
| 2007/0197890 A1 | 8/2007 | Boock et al. |
| 2007/0299617 A1* | 12/2007 | Willis ............... A61B 5/7225 204/403.01 |
| 2008/0108942 A1 | 5/2008 | Brister et al. |
| 2008/0119703 A1 | 5/2008 | Brister et al. |
| 2008/0156661 A1* | 7/2008 | Cooper ............... A61B 5/6848 204/412 |
| 2010/0030045 A1* | 2/2010 | Gottlieb ............... A61B 5/1473 600/347 |
| 2010/0196203 A1 | 8/2010 | Sanghera et al. |
| 2011/0024307 A1 | 2/2011 | Simpson et al. |
| 2011/0040163 A1* | 2/2011 | Telson ............... A61B 5/14532 600/347 |
| 2012/0003687 A1 | 1/2012 | Toner et al. |
| 2012/0004524 A1 | 1/2012 | Van Antwerp et al. |
| 2012/0262298 A1 | 10/2012 | Böhm et al. |
| 2012/0265037 A1 | 10/2012 | Bohm et al. |
| 2013/0245981 A1 | 9/2013 | Estes et al. |
| 2014/0005509 A1* | 1/2014 | Bhavaraju ............ A61B 5/7278 600/347 |
| 2014/0046155 A1* | 2/2014 | Hayter ................ A61B 5/1468 600/309 |
| 2015/0351672 A1 | 12/2015 | Vanslyke et al. |
| 2016/0290957 A1* | 10/2016 | Ram .................... A61B 5/1477 |
| 2017/0181672 A1 | 6/2017 | Nogueira et al. |
| 2017/0184527 A1 | 6/2017 | Nogueira et al. |
| 2017/0228345 A1* | 8/2017 | Gupta .................. G06F 17/141 |
| 2017/0281092 A1* | 10/2017 | Burnette .............. A61B 5/1473 |
| 2017/0311852 A1* | 11/2017 | Morgan ............ A61B 5/14865 |
| 2018/0279928 A1 | 10/2018 | Previl |
| 2018/0325430 A1 | 11/2018 | Vaddiraju et al. |
| 2018/0372667 A1 | 12/2018 | Gupta |
| 2019/0004005 A1* | 1/2019 | Oja .................... G01N 27/3272 |
| 2019/0227022 A1* | 7/2019 | Harley-Trochimczyk .................. A61B 5/01 |

FOREIGN PATENT DOCUMENTS

| | | | |
|---|---|---|---|
| JP | 2015509803 A | 4/2015 | |
| WO | WO-2012154548 A1 * | 11/2012 | ......... A61B 5/14532 |
| WO | WO-2019007842 A1 * | 1/2019 | ......... A61B 5/14532 |

* cited by examiner

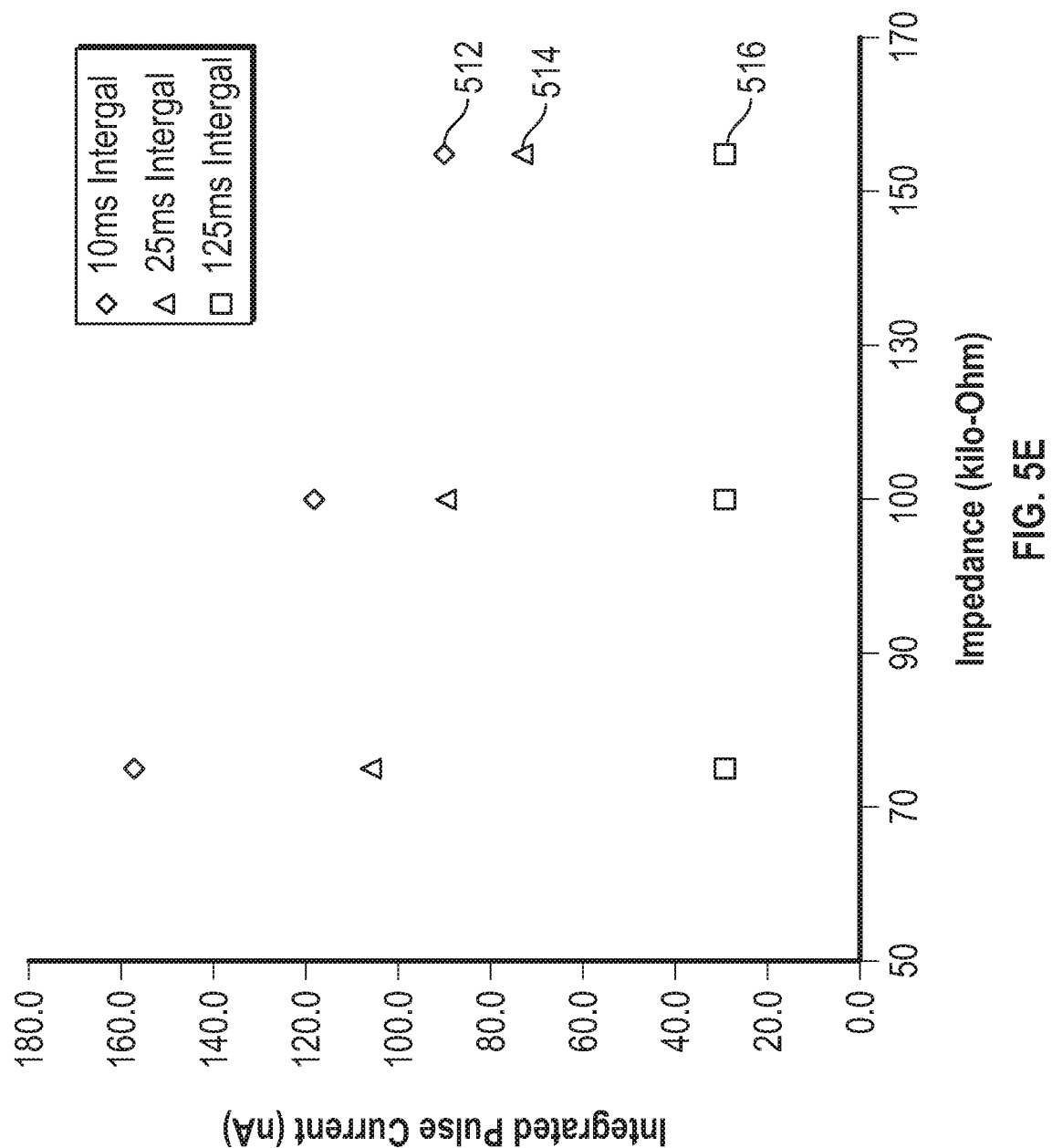

| Algo | MARD Percentiles | | | RMSE (pA/mg/dL) | % RMSE |
|---|---|---|---|---|---|
| | 2.5%-tile | Median | 97.5%-tile | | |
| FC | 10.21 | 11.66 | 13.38 | 4.88 | 15.36 |
| FC Local | 8.98 | 10.20 | 11.33 | 4.30 | 14.62 |
| Impd | 9.12 | 10.29 | 11.53 | 4.35 | 14.84 |
| Impd+cc | 8.92 | 10.12 | 11.29 | 4.27 | 14.55 |
| Impd+T | 8.70 | 9.87 | 11.14 | 4.28 | 14.60 |
| Impd+T+cc | 8.04 | 9.38 | 10.69 | 4.11 | 13.97 |

ANALYTE SENSOR WITH IMPEDANCE DETERMINATION

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application Ser. No. 62/786,166, filed on Dec. 28, 2018, U.S. Provisional Application Ser. No. 62/786,116, filed on Dec. 28, 2018, U.S. Provisional Application Ser. No. 62/786,208, filed on Dec. 28, 2018, U.S. Provisional Application Ser. No. 62/786,127, filed on Dec. 28, 2018, and U.S. Provisional Application Ser. No. 62/786,228, filed on Dec. 28, 2018. Each of the aforementioned applications is incorporated by reference herein in its entirety, and each is hereby expressly made a part of this specification.

TECHNICAL FIELD

The present development relates generally to medical devices such as analyte sensors, and more particularly, but not by way of limitation, to systems, devices, and methods that use impedance measurements in a continuous glucose monitoring system.

BACKGROUND

Diabetes is a metabolic condition relating to the production or use of insulin by the body. Insulin is a hormone that allows the body to use glucose for energy, or store glucose as fat.

When a person eats a meal that contains carbohydrates, the food is processed by the digestive system, which produces glucose in the person's blood. Blood glucose can be used for energy or stored as fat. The body normally maintains blood glucose levels in a range that provides sufficient energy to support bodily functions and avoids problems that can arise when glucose levels are too high, or too low. Regulation of blood glucose levels depends on the production and use of insulin, which regulates the movement of blood glucose into cells.

When the body does not produce enough insulin, or when the body is unable to effectively use insulin that is present, blood sugar levels can elevate beyond normal ranges. The state of having a higher than normal blood sugar level is called "hyperglycemia." Chronic hyperglycemia can lead to a number of health problems, such as cardiovascular disease, cataract and other eye problems, nerve damage (neuropathy), and kidney damage. Hyperglycemia can also lead to acute problems, such as diabetic ketoacidosis—a state in which the body becomes excessively acidic due to the presence of blood glucose and ketones, which are produced when the body cannot use glucose. The state of having lower than normal blood glucose levels is called "hypoglycemia." Severe hypoglycemia can lead to acute crises that can result in seizures or death.

A diabetes patient can receive insulin to manage blood glucose levels. Insulin can be received, for example, through a manual injection with a needle. Wearable insulin pumps are also available. Diet and exercise also affect blood glucose levels. A glucose sensor can provide an estimated glucose concentration level, which can be used as guidance by a patient or caregiver.

Diabetes conditions are sometimes referred to as "Type 1" and "Type 2." A Type 1 diabetes patient is typically able to use insulin when it is present, but the body is unable to produce sufficient amounts of insulin, because of a problem with the insulin-producing beta cells of the pancreas. A Type 2 diabetes patient may produce some insulin, but the patient has become "insulin resistant" due to a reduced sensitivity to insulin. The result is that even though insulin is present in the body, the insulin is not sufficiently used by the patient's body to effectively regulate blood sugar levels.

Blood sugar concentration levels may be monitored with an analyte sensor, such as a continuous glucose monitor. A continuous glucose monitor may provide the wearer (patient) with information, such as an estimated blood glucose level or a trend of estimated blood glucose levels.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

This present application discloses, among other things, systems, devices, and methods for use of impedance or conductance measurements or estimates in an analyte sensor, such as a glucose sensor.

Example 1 is a method comprising disconnecting an analyte sensor from a measurement circuit and reconnecting the analyte sensor to the measurement circuit after an accumulation period. The subject matter of Example 1 may also comprise receiving a signal from the analyte sensor, where the signal is indicative of an amount of charge accumulated on the analyte sensor during the accumulation period. The subject matter of Example 1 may further comprise determining an estimated analyte concentration level based on the received signal.

In Example 2, the subject matter of Example 1 optionally includes using a gate circuit to disconnect and reconnect the analyte sensor.

In Example 3, the subject matter of any one or more of Examples 1-2 optionally includes determining a membrane status based on the analyte signal received after reconnection of the analyte sensor to the measurement circuit.

In Example 4, the subject matter of any one or more of Examples 1-3 optionally includes wherein the disconnection and reconnection of the analyte sensor improves a signal to interference ratio of the analyte sensor.

In Example 5, the subject matter of any one or more of Examples 1-4 optionally includes measuring an open cell potential during the accumulation period and determining a membrane status based on one or more open cell potentials.

In Example 6, the subject matter of any one or more of Examples 3-5 optionally includes wherein the membrane status includes an interference status.

In Example 7, the subject matter of any one or more of Examples 3-6 optionally includes wherein the membrane status includes a damage or defect status.

In Example 8, the subject matter of Example 7 optionally includes monitoring a current profile after reconnecting the analyte sensor and detecting a membrane fault using the current profile.

In Example 9, the subject matter of any one or more of Examples 7-8 optionally includes determining an impedance characteristic and detecting a membrane fault responsive to the impedance characteristic satisfying a condition.

In Example 10, the subject matter of Example 9 optionally includes wherein the impedance characteristic is an estimated membrane impedance, a first derivative of impedance, a second derivative impedance, or a fitted curve.

Example 11 is a continuous analyte sensor comprising an analyte sensor and sensor electronics operatively coupled to the analyte sensor to receive a signal indicative of glucose concentration from the analyte sensor. The sensor electronics may comprise a measurement circuit. The sensor electronics may disconnect the measurement circuit from the analyte sensor and reconnect the analyte sensor to the measurement circuit after an accumulation period. The measurement circuit may measure an accumulated charge from the analyte sensor after reconnection of the analyte sensor to the measurement circuit.

In Example 12, the subject matter of Example 11 optionally includes the sensor electronics determining an estimated analyte concentration level based on the measurement of the accumulated charge.

In Example 13, the subject matter of any one or more of Examples 11-12 optionally includes the sensor electronics comprising a gate circuit to disconnect and reconnect the analyte sensor from the measurement circuit.

In Example 14, the subject matter of any one or more of Examples 11-13 optionally includes the sensor electronics determining a membrane status based on a profile of an analyte signal received after reconnection of the analyte sensor to the measurement circuit.

In Example 15, the subject matter of any one or more of Examples 11-14 optionally includes the disconnection and reconnection of the analyte sensor improving a signal to interference ratio of the analyte sensor.

In Example 16, the subject matter of any one or more of Examples 11-15 optionally includes the sensor electronics measuring an open cell potential during a period of time that the analyte sensor is disconnected and determining a membrane status based on a profile of the open cell potential.

In Example 17, the subject matter of any one or more of Examples 14-16 optionally includes the membrane status including an interference status.

In Example 18, the subject matter of any one or more of Examples 14-17 optionally includes the membrane status including a damage or defect status.

In Example 19, the subject matter of Example 18 optionally includes the sensor electronics monitoring a current profile of the signal received from the analyte sensor after reconnecting the analyte sensor and detecting a membrane fault using the current profile.

In Example 20, the subject matter of any one or more of Examples 18-19 optionally includes the sensor electronics determining an impedance characteristic and detect a membrane fault responsive to the impedance characteristic satisfying a condition.

Example 21 is a method comprising applying a biphasic pulse to a continuous analyte sensor circuit, integrating a current response to the biphasic pulse, and determining an estimated impedance using the integrated current response.

In Example 22, the subject matter of any one or more of Examples 1-21 optionally includes compensating a sensor sensitivity using the determined impedance.

In Example 23, the subject matter of Example 22 optionally includes determining impedance using a signal at a frequency that avoid an effect of a double-layer membrane capacitance on the impedance.

In Example 24, the subject matter of any one or more of Examples 22-23 optionally includes wherein compensation is based on impedance and one or more additional factors.

In Example 25, the subject matter of Example 24 optionally includes the one or more additional factors including temperature, a calibration curve, or both.

In Example 26, the subject matter of Example 25 optionally includes the compensation using a transmitter temperature, and the transmitter temperature is filtered using Green's function.

In Example 27, the subject matter of any one or more of Examples 1-26 optionally includes using the determined impedance to determine humidity of an environment of the sensor.

In Example 28, the subject matter of Example 27 optionally includes detection of humidity during transportation of the sensor.

In Example 29, the subject matter of any one or more of Examples 27-28 optionally includes detection of humidity during storage of the sensor.

In Example 30, the subject matter of any one or more of Examples 27-29 optionally includes compensating a sensor sensitivity based upon the determined humidity.

In Example 31, the subject matter of any one or more of Examples 27-30 optionally includes declaring an alert based upon a determined humidity.

In Example 32, the subject matter of Example 31 optionally includes delivering an alert using a smart device to alert a user that a sensor should not be used due to excessive humidity exposure.

An example (e.g., "Example 9") of subject matter (e.g., a system or apparatus) may optionally combine any portion or combination of any portion of any one or more of Examples 1-8 to include "means for" performing any portion of any one or more of the functions or methods of Examples 1-8.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments described in the present document.

FIG. 5E is a graph that shows integrated pulse current plotted against impedance for three different integration times.

FIG. 10G provides data that shows the performance improvement achieved by various compensation techniques described above.

DETAILED DESCRIPTION

The present inventors have recognized, among other things, that measurements or estimates of impedance in an analyte sensor system may be used to improve the operation of the analyte sensor system. For example, impedance may be used to improve the performance (e.g., accuracy or precision) of an analyte sensor system, or to detect damage or a fault in a sensor. In some examples, an estimate of the impact (e.g., effective capacitance) of a membrane layer interface may be determined.

Overview

An estimate of an impedance of a sensor (e.g., double-layer impedance of a membrane) may be determined using electronic measurements. The impedance estimate may be used, for example, to calibrate a sensor, compensate for drift, identify a damaged sensor, compensate for damage or deviation from a performance standard (e.g., default sensitivity curve).

Impedance may also be used to reduce or eliminate a need for in vivo sensor calibration using blood glucose meter (e.g., "finger stick") data. An analyte sensor, such as a glucose sensor, may be calibrated during manufacture ("factory calibration"), to provide a predictable analyte response curve. For example, a sensor's response to the presence of an analyte (e.g., a glucose concentration) may be checked during (or after) manufacture to assure that the sensor's response to the analyte (e.g., the current signal generated in response to exposure to a known glucose concentration) is within an acceptable range. After implantation in the body, the analyte sensitivity of a sensor is subject to change over time, i.e. "drift." One approach to accounting for in vivo drift is to periodically calibrate the sensor using information from a blood glucose meter (i.e., "finger stick" blood glucose measurements). However, it may be desirable to avoid use of blood glucose meter data or reduce the number or frequency of such in-vivo calibration events. For reasons described in detail below, determining one or more impedance values (e.g., for the circuit 400 shown in FIG. 4) may reduce or eliminate the need to rely on blood glucose meter information. In some examples, impedance may allow for factory calibration, without further in vivo calibration events.

Figure 3A:
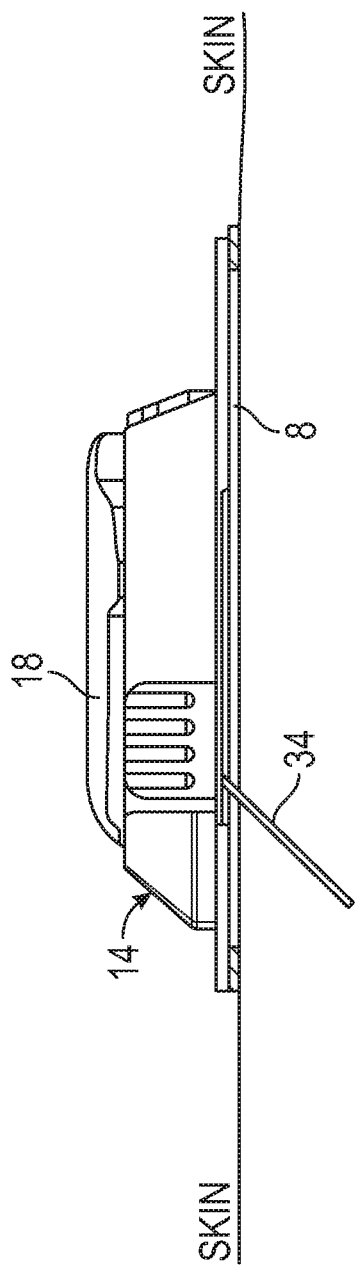
FIG. 3A is an illustration of an example analyte sensor system.
Figure 3C:
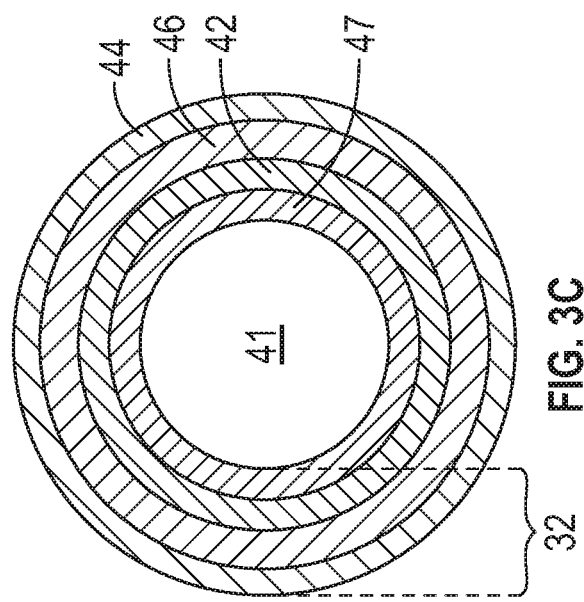
FIG. 3C is a cross-sectional view of the analyte sensor of FIG. 3B.

An analyte sensor may include a number of domains or layers, which may include a diffusion resistance domain (e.g., domain 44 shown in FIG. 3C). In a glucose sensor, for example, the diffusion coefficient of electrically neutral glucose molecules in the resistance layer may be a direct correlate or determinant of glucose sensitivity. The electrochemical impedance of the resistance layer is a measure of the mobility of electrically charged ions in the resistance layer. Although the diffusion coefficient and electrochemical impedance are two fundamentally different physical properties associated with two different agents (glucose vs. ions), bench experiments have shown these properties to correlate with each other. As a result, the electrochemical impedance may be used as a surrogate to estimate the diffusion coefficient, which may allow for compensations in in vivo drift of glucose sensitivity. For example, a sensor compensation may be based upon a membrane impedance determined from circuit measurements made in vivo or prior to implantation.

As further described in detail below, the impedance of the membrane (e.g., the electrochemical impedance of the resistance layer) may be determined or estimated based on electrical measurements by sensor electronics or other instrumentation. In various examples, an impedance measurement may be obtained using a sine-wave approach, a step response function approach, or an impulse response function approach. A sine-wave approach may include imposing sinusoidal perturbations in the bias voltage over the RL and measuring the amplitudes of sinusoidal response currents: a scan through a band of frequencies may be performed, and the ratio between the voltage and current excursions may be taken as the impedance at a specific frequency. In step response function approach, a square step change in the bias may be imposed and held, and a perturbation in the sensor current may be measured: the ratio between the Fourier or Laplace transform of the step voltage and that of the transient current is the impedance of the membrane. In an impulse response function approach, a short square wave pulse in the bias voltage may be imposed, and a perturbation in the sensor current may be measured. The impedance may be determined from the current perturbation and the applied bias voltage pulse.

The sensor sensitivity ($m_t$) correlates linearly with the reciprocal of the membrane impedance ($Z_{RL,t}$), i.e. ZRL, $t^*m_t$=constant. This relationship can be employed to make use of impedance for estimating in vivo sensitivity in real time:

$$\hat{m}_t = Z_{RL,t}^{-1} \cdot \text{constant}$$

Based on this relationship, a sensor may be calibrated in vivo, which may allow for compensation for drift after deployment in a host.

In some examples, a sensor elapsed time (t) since insertion and an impedance ($R_t$) determined from measurements at the elapsed time may be used as input for a function to estimate sensitivity, e.g., sensitivity ($m_t$) of the sensor may be provided by the function $m_t=f(t)/R_t$. In some examples, an initial calibration curve (CC) may also be used to determine an estimated sensor sensitivity, e.g., $m_t=f(CC, t)/R_t$.

An estimated sensor sensitivity may be used to determine an estimated analyte concentration (e.g., estimated glucose concentration) based upon sensor output (e.g., a current or charge count from a working electrode measured using sensor electronics) and the sensor sensitivity ($m_t$) estimated using the impedance.

Testing and experimentation have been conducted to establish and verify techniques for improving performance of analyte sensor systems, mitigating the effect of double-layer capacitance effects, and detecting, quantifying, or compensating for damage or abnormalities in a sensor membrane. Data, charts, and examples are provided to assist with describing the present subject matter.

Impedance characteristics of a sensor may be used to detect or determine (e.g., quantify) an amount of damage or manufacturing abnormality (e.g., membrane imperfection) in a sensor. A sensor may be functional even though a membrane may include minor imperfections that may be identifiable under a microscope. Some sensors with extensive damage or major manufacturing abnormalities may provide unacceptable performance. Identification of such sensors may provide an opportunity to remove a sensor from circulation or compensate an estimated analyte concentration based on an understanding of impedance characteristics of the sensor. In some examples, a combination of characteristics may be used to assess the integrity of a sensor membrane, e.g., to identify sensors with damage or abnormality, or characterize the extent of sensor abnormality or damage. For example, impedance may be used in combination with dual frequency impedance (e.g., impedance 100 Hz and 1000 Hz), or impedance may be used in combination with an impedance trend or time-based variable (e.g., impedance difference at different points in time), or impedance difference at different frequencies may be used in combination with impedance difference at different points in time (e.g., 72 seconds and 180 seconds or low point and a stable point.) In other examples, other variables, such as signal variability (e.g., perceived noise level), or response to a voltage change (e.g., rate of impedance change) may also be used in combination with any of the above factors and combinations.

In certain situations, such as accidently bumping an analyte sensor, catching a sensor base on an object, or "tenting" of an adhesive patch (e.g., when portions of the adhesive patch are not completely adhered to the skin) to which a sensor is attached, an analyte sensor may be partially pulled out of the skin or otherwise dislodged, which may result in an inaccurate sensor reading. Such an event may be detected based upon a change in impedance.

Sensor impedance may depend on the insertion depth of the sensor into a host. If a sensor is retracted a significant distance, a step change in sensor impedance may be observed.

In an example, an impedance may be measured after insertion, and subsequently measured after insertion. For example, the impedance may be measured recurrently, or may be measured responsive to detection of an event, such as a potential dislodgement event, which may for example be detected using an accelerometer in sensor electronics, or from other sensor information. A sudden change in impedance may indicate dislodgment. For example, a determined impedance change greater than a predetermined impedance change (e.g., in ohms) over a predetermined time period may indicate a dislodgement event. In some examples, a system may declare an alert or raise a "replace sensor" alarm" responsive to detection of a sudden change in impedance.

In some examples, factory calibration may be improved by using impedance for factory calibration. Impedance may be used to determine a calibration value or curve for a sensor, or verification that a sensitivity of the sensor is within acceptable limits. Without use of impedance, calibration may require sequentially exposing a sensor to immersion in fluid baths having varying levels of analyte concentration (e.g., varying glucose concentrations), while applying a bias potential, which may be complicated, time consuming, expensive, or difficult to scale. In some examples, impedance may be used as a replacement (or compliment) to such soaking in analyte solutions.

In an example, a sensor may be pre-soaked in a solution to facilitate measurement of impedance. An impedance measurement may then be made. In an example, the impedance determination (e.g., using current measurements described above) may take one minute, or less, in contrast to a typical one-hour measurement process of current measurements in response to analyte concentrations. This approach may be desirable, for example, because the process does not require application of a bias potential, and a large number of sensors may be soaked simultaneously. In an example, an eight-channel potentiostat may be used to simultaneously measure the impedance of eight sensors on a single fixture. In some examples, the determined impedance values may be used to determine a sensor sensitivity or confirm that the sensor sensitivity or impedance is within defined limits, or to predict drift or later estimate in vivo drift, e.g., using in vivo impedance determinations, which may be compared to the factory impedance values or a default value or range.

In some examples, a sensor may be pre-screened using an impedance procedure, so that damaged sensors may be identified and removed from a production process, which may improve sensor accuracy statistics (e.g., reduce MARD), or improve process efficiency by reducing the number of sensors that proceed through a conventional bath calibration process.

Example System

Figure 1:
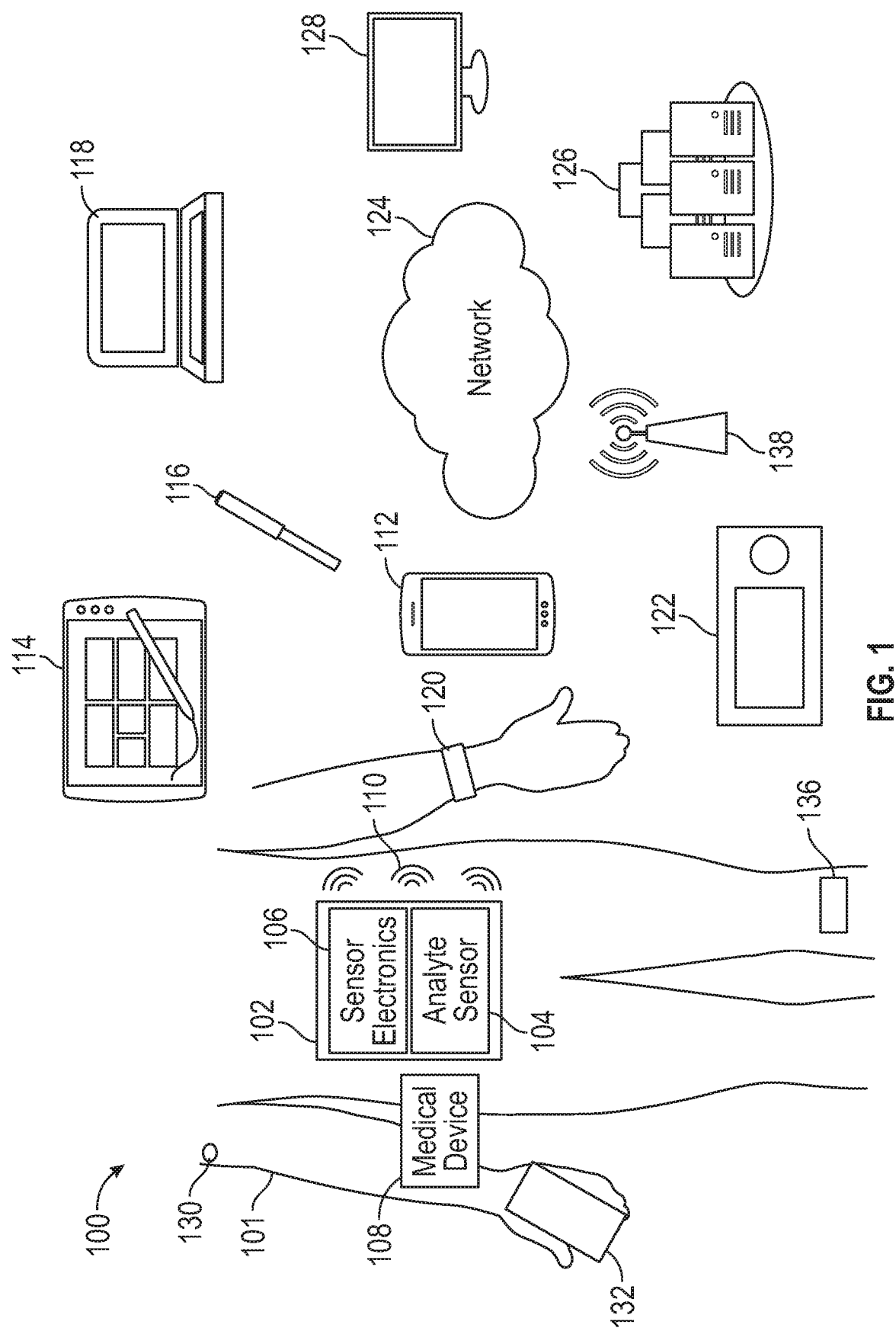
FIG. 1 is an illustration of an example medical device system.

FIG. 1 is an illustration of an example system 100. The system 100 may include an analyte sensor system 102 that may be coupled to a host 101. The host 101 may be a human patient. The patient may, for example, be subject to a temporary or permanent diabetes condition or other health condition for which analyte monitoring may be useful.

The analyte sensor system 102 may include an analyte sensor 104, which may for example be a glucose sensor. The glucose sensor may be any device capable of measuring the concentration of glucose. For example, the analyte sensor 104 may be fully implantable, or the analyte sensor 104 may be wearable on the body (e.g., on the body but not under the skin), or the analyte sensor 104 may be a transcutaneous device (e.g., with a sensor residing under or in the skin of a host). It should be understood that the devices and methods described herein can be applied to any device capable of detecting a concentration of glucose and providing an output signal that represents the concentration of glucose (e.g., as a form of analyte data).

The analyte sensor system 102 may also include sensor electronics 106. In some examples, the analyte sensor 104 and sensor electronics 106 may be provided as an integrated package. In other examples, the analyte sensor 104 and sensor electronics 106 may be provided as separate components or modules. For example, the analyte sensor system 102 may include a disposable (e.g., single-use) base that may include the analyte sensor 104, a component for attaching the sensor 104 to a host (e.g., an adhesive pad), or a mounting structure configured to receive another component. The system 102 may also include a sensor electronics package, which may include some or all of the sensor electronics 106 shown in FIG. 2. The sensor electronics package may be reusable.

An analyte sensor 104 may use any known method, including invasive, minimally-invasive, or non-invasive sensing techniques (e.g., optically excited fluorescence, microneedle, transdermal monitoring of glucose), to provide a data stream indicative of the concentration of the analyte in a host 101. The data stream may be a raw data signal, which may be converted into a calibrated and/or filtered data stream that is used to provide a useful value of the analyte (e.g., estimated blood glucose concentration level) to a user, such as a patient or a caretaker (e.g., a parent, a relative, a guardian, a teacher, a doctor, a nurse, or any other individual that has an interest in the wellbeing of the host 101).

Analyte sensor 104 may, for example, be a continuous glucose sensor, which may, for example, include a subcutaneous, transdermal (e.g., transcutaneous), or intravascular device. In some embodiments, such a sensor or device may recurrently (e.g., periodically or intermittently) analyze sensor data. The glucose sensor may use any method of glucose measurement, including enzymatic, chemical, physical, electrochemical, spectrophotometric, polarimetric, calorimetric, iontophoretic, radiometric, immunochemical, and the like. In various examples, the analyte sensor system 102 may be or include a continuous glucose monitor sensor available from DexCom™, (e.g., the DexCom G5™ sensor or Dexcom G6™ sensor or any variation thereof), from Abbott™ (e.g., the Libre™ sensor), or from Medtronic™ (e.g., the Enlite™ sensor).

In some examples, analyte sensor 104 may be an implantable glucose sensor, such as described with reference to U.S. Pat. No. 6,001,067 and U.S. Patent Publication No. US-2005-0027463-A1, which are incorporated by reference. In some examples, analyte sensor 104 may be a transcutaneous glucose sensor, such as described with reference to U.S. Patent Publication No. US-2006-0020187-A1, which is incorporated by reference. In some examples, analyte sensor 104 may be configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007, all of which are incorporated by reference. In some examples, the continuous glucose sensor may include a transcutaneous sensor such as described in U.S. Pat. No. 6,565,509 to Say et al., which is incorporated by reference. In some examples, analyte sensor 104 may be a continuous glucose sensor that includes a subcutaneous sensor such as described with reference to U.S. Pat. No. 6,579,690 to Bonnecaze et al. or U.S. Pat. No. 6,484,046 to Say et al., which are incorporated by reference. In some examples, the continuous glucose sensor may include a refillable subcutaneous sensor such as described with reference to U.S. Pat. No. 6,512,939 to Colvin et al., which is incorporated by reference. The continuous glucose sensor may include an intravascular sensor such as described with reference to U.S. Pat. No. 6,477,395 to Schulman et al., which is incorporated by reference. The continuous glucose sensor may include an intravascular sensor such as described with reference to U.S. Pat. No. 6,424,847 to Mastrototaro et al., which is incorporated by reference.

The system 100 may also include a second medical device 108, which may, for example, be a drug delivery device (e.g., insulin pump or insulin pen). In some examples, the medical device 108 may be or include a sensor, such as another analyte sensor 104, a heart rate sensor, a respiration sensor, a motion sensor (e.g. accelerometer), posture sensor (e.g. 3-axis accelerometer), acoustic sensor (e.g. to capture ambient sound or sounds inside the body). In some examples, medical device 108 may be wearable, e.g., on a watch, glasses, contact lens, patch, wristband, ankle band, or other wearable item, or may be incorporated into a handheld device (e.g., a smartphone). In some examples, the medical device 108 may include a multi-sensor patch that may, for example, detect one or more of an analyte level (e.g., glucose, lactate, insulin or other substance), heart rate, respiration (e.g., using impedance), activity (e.g., using an accelerometer), posture (e.g., using an accelerometer), galvanic skin response, tissue fluid levels (e.g., using impedance or pressure).

The analyte sensor system 102 may communicate with the second medical device 108 via a wired connection, or via a wireless communication signal 110. For example, the analyte sensor system 102 may be configured to communicate using via radio frequency (e.g., Bluetooth, Medical Implant Communication System (MICS), Wi-Fi, NFC, RFID, Zigbee, Z-Wave or other communication protocols), optically (e.g., infrared), sonically (e.g., ultrasonic), or a cellular protocol (e.g., CDMA (Code Division Multiple Access) or GSM (Global System for Mobiles)), or via a wired connection (e.g., serial, parallel, etc.).

The system 100 may also include a wearable sensor 130, which may include a sensor circuit (e.g., a sensor circuit configured to detect a glucose concentration or other analyte concentration) and a communication circuit, which may, for example, be a near field communication (NFC) circuit. In some examples, information from the wearable sensor 130 may be retrieved from the wearable sensor 130 using a user device 132 such as a smart phone that is configured to communicate with the wearable sensor 130 via NFC when the user device 132 is placed near the wearable sensor 130 (e.g., swiping the user device 132 over the sensor 130 retrieves sensor data from the wearable sensor 130 using NFC). The use of NFC communication may reduce power consumption by the wearable sensor 130, which may reduce the size of a power source (e.g., battery or capacitor) in the wearable sensor 130 or extend the usable life of the power source. In some examples, the wearable sensor 130 may be wearable on an upper arm as shown. In some examples, a wearable sensor 130 may additionally or alternatively be on the upper torso of the patient (e.g., over the heart or over a lung), which may, for example, facilitate detecting heart rate, respiration, or posture. A wearable sensor 136 may also be on the lower body (e.g., on a leg).

In some examples, an array or network of sensors may be associated with the patient. For example, one or more of the analyte sensor system 102, medical device 108, wearable device 120 such as a watch, and an additional wearable sensor 130 may communicate with one another via wired or wireless (e.g., Bluetooth, MICS, NFC or any of the other options described above,) communication. The additional wearable sensor 130 may be any of the examples described above with respect to medical device 108. The analyte sensor system 102, medical device 108, and additional sensor 130 on the host 101 are provided for the purpose of illustration and description and are not necessarily drawn to scale.

The system 100 may also include one or more peripheral devices, such as a hand-held smart device (e.g., smartphone) 112, tablet 114, smart pen 116 (e.g., insulin delivery pen with processing and communication capability), computer 118, a wearable device 120 such as a watch, or peripheral medical device 122 (which may be a proprietary device such as a proprietary user device available from DexCom), any of which may communicate with the analyte sensor system 102 via a wireless communication signal 110, and may also communicate over a network 124 with a server system (e.g., remote data center) 126 or with a remote terminal 128 to facilitate communication with a remote user (not shown) such as a technical support staff member or a clinician.

The wearable device 120 may include an activity sensor, a heart rate monitor (e.g., light-based sensor or electrode-based sensor), a respiration sensor (e.g., acoustic- or electrode-based), a location sensor (e.g., GPS), or other sensors.

The system 100 may also include a wireless access point (WAP) 138 that may be used to communicatively couple one or more of analyte sensor system 102, network 124, server system 126, medical device 108 or any of the peripheral devices described above. For example, WAP 138 may provide Wi-Fi and/or cellular connectivity within system 100. Other communication protocols (e.g., Near Field Communication (NFC) or Bluetooth) may also be used among devices of the system 100. In some examples, the server system 126 may be used to collect analyte data from analyte sensor system 102 and/or the plurality of other devices, and to perform analytics on collected data, generate or apply universal or individualized models for glucose levels, and communicate such analytics, models, or information based thereon back to one or more of the devices in the system 100.

Figure 2:
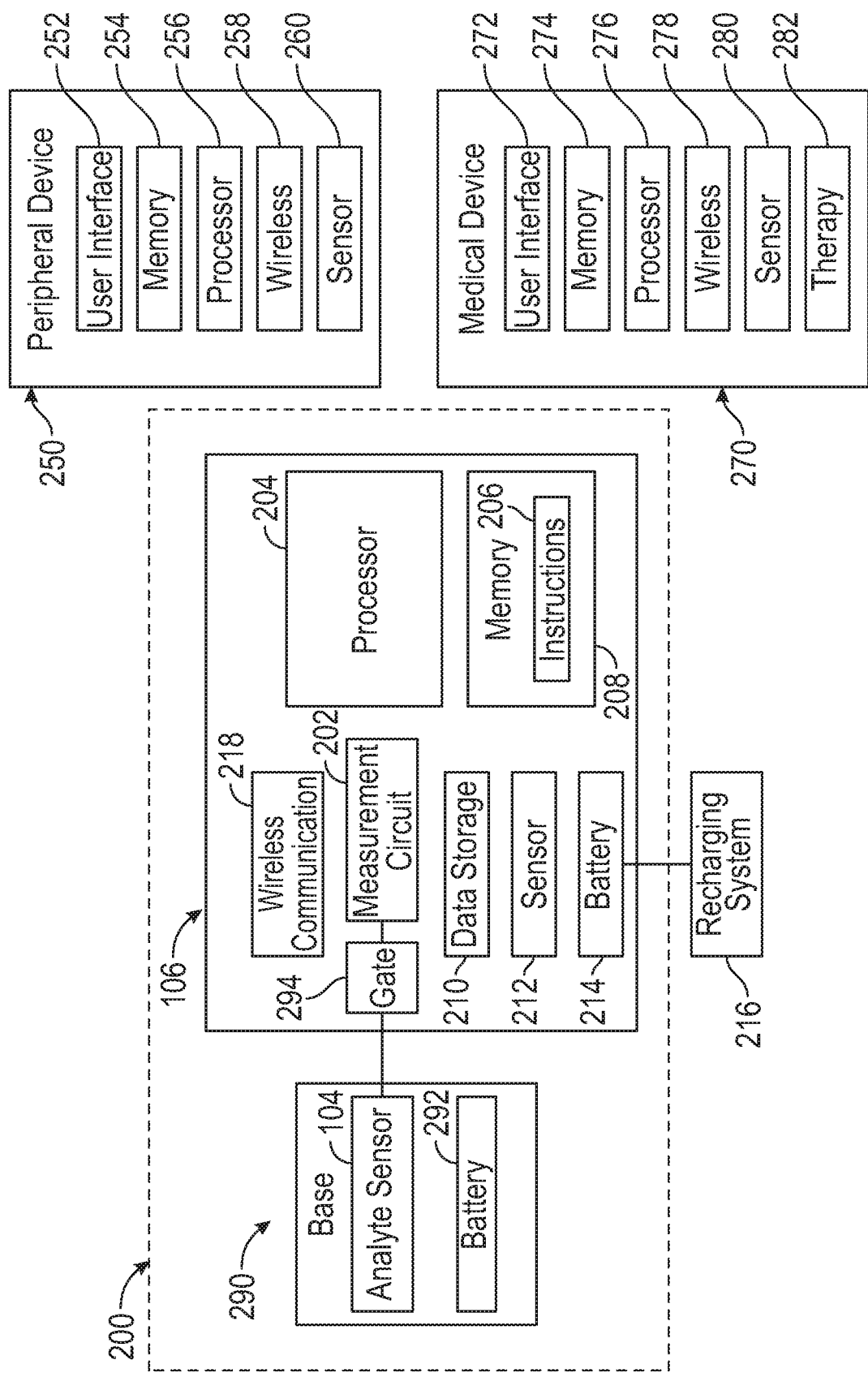
FIG. 2 is a schematic illustration of various example electronic components that may be part of the medical device system shown in FIG. 1.

FIG. 2 is a schematic illustration of various example electronic components that may be part of a medical device system 200. In an example, the system 200 may include sensor electronics 106 and a base 290. While a specific example of division of components between the base 290 and sensor electronics 106 is shown, it is understood that some examples may include additional components in the base 290 or in the sensor electronics 106, and that some of the components (e.g., a battery or supercapacitor) that are shown in the sensor electronics 106 may be alternatively or additionally (e.g., redundantly) provided in the base 290.

In an example, the base 290 may include the analyte sensor 104 and a battery 292. In some examples, the base 290 may be replaceable, and the sensor electronics 106 may include a debouncing circuit (e.g., gate with hysteresis or delay) to avoid, for example, recurrent execution of a power-up or power down process when a battery is repeatedly connected and disconnected or avoid processing of noise signal associated with removal or replacement of a battery.

The sensor electronics 106 may include electronics components that are configured to process sensor information, such as sensor data, and generate transformed sensor data and displayable sensor information. The sensor electronics 106 may, for example, include electronic circuitry associated with measuring, processing, storing, or communicating continuous analyte sensor data, including prospective algorithms associated with processing and calibration of the sensor data. The sensor electronics 106 may include hardware, firmware, and/or software that enables measurement of levels of the analyte via a glucose sensor. Electronic components may be affixed to a printed circuit board (PCB), or the like, and can take a variety of forms. For example, the electronic components may take the form of an integrated circuit (IC), such as an Application-Specific Integrated Circuit (ASIC), a microcontroller, and/or a processor.

As shown in FIG. 2, the sensor electronics 106 may include a measurement circuit 202 (e.g., potentiostat), which may be coupled to the analyte sensor 104 and configured to recurrently obtain analyte sensor readings using the analyte sensor 104, for example by continuously or recurrently measuring a current flow indicative of analyte concentration. The sensor electronics 106 may include a gate circuit 294, which may be used to gate the connection between the measurement circuit 202 and the analyte sensor 104. In an example, the analyte sensor 104 accumulates charge over an accumulation period, and the gate circuit 294 is opened so that the measurement circuit 202 can measure the accumulated charge. Gating the analyte sensor 104 may improve the performance of the sensor system 102 by creating a larger signal to noise or interference ratio (e.g., because charge accumulates from an analyte reaction, but sources of interference, such as the presence of acetaminophen near a glucose sensor, do not accumulate, or accumulate less than the charge from the analyte reaction). The sensor electronics 106 may also include a processor 204, which may retrieve instructions 206 from memory 208 and execute the instructions 206 to determine control application of bias potentials to the analyte sensor 104 via the potentiostat, interpret signals from the sensor 104, or compensate for environmental factors. The processor 204 may also save information in data storage memory 210 or retrieve information from data storage memory 210. In various examples, data storage memory 210 may be integrated with memory 208, or may be a separate memory circuit, such as a non-volatile memory circuit (e.g., flash RAM). Examples of systems and methods for processing sensor analyte data are described in more detail herein and in U.S. Pat. Nos. 7,310,544 and 6,931,327.

The sensor electronics 106 may also include a sensor 212, which may be coupled to the processor 204. The sensor 212 may be a temperature sensor, accelerometer, or another suitable sensor. The sensor electronics 106 may also include a power source such as a capacitor or battery 214, which may be integrated into the sensor electronics 106, or may be removable, or part of a separate electronics package. The battery 214 (or other power storage component, e.g., capacitor) may optionally be rechargeable via a wired or wireless (e.g., inductive or ultrasound) recharging system 216. The recharging system 216 may harvest energy or may receive energy from an external source or on-board source. In various examples, the recharge circuit may include a triboelectric charging circuit, a piezoelectric charging circuit, an RF charging circuit, a light charging circuit, an ultrasonic charging circuit, a heat charging circuit, a heat harvesting circuit, or a circuit that harvests energy from the communication circuit. In some examples, the recharging circuit may recharge the rechargeable battery using power supplied from a replaceable battery (e.g., a battery supplied with a base component).

The sensor electronics 106 may also include one or more supercapacitors in the sensor electronics package (as shown), or in the base 290. For example, the supercapacitor may allow energy to be drawn from the battery 214 in a highly consistent manner to extend the life of the battery 214. The battery 214 may recharge the supercapacitor after the supercapacitor delivers energy to the communication circuit or to the processor 204, so that the supercapacitor is prepared for delivery of energy during a subsequent high-load period. In some examples, the supercapacitor may be configured in parallel with the battery 214. A device may be configured to preferentially draw energy from the supercapacitor, as opposed to the battery 214. In some examples, a supercapacitor may be configured to receive energy from a rechargeable battery for short-term storage and transfer energy to the rechargeable battery for long-term storage.

The supercapacitor may extend an operational life of the battery 214 by reducing the strain on the battery 214 during the high-load period. In some examples, a supercapacitor removes at least 10% of the strain off the battery during high-load events. In some examples, a supercapacitor removes at least 20% of the strain off the battery during high-load events. In some examples, a supercapacitor removes at least 30% of the strain off the battery during high-load events. In some examples, a supercapacitor removes at least 50% of the strain off the battery during high-load events.

The sensor electronics 106 may also include a wireless communication circuit 218, which may for example include a wireless transceiver operatively coupled to an antenna. The wireless communication circuit 218 may be operatively coupled to the processor 204 and may be configured to wirelessly communicate with one or more peripheral devices or other medical devices, such as an insulin pump or smart insulin pen.

A peripheral device 250 may, for example, be a wearable device (e.g., activity monitor), such as a wearable device 120. In other examples, the peripheral device 250 may be a hand-held smart device 112 (e.g., smartphone or other device such as a proprietary handheld device available from Dexcom), a tablet 114, a smart pen 116, or special-purpose computer 118 shown in FIG. 1.

The peripheral device 250 may include a user interface 252, a memory circuit 254, a processor 256, a wireless communication circuit 258, a sensor 260, or any combination thereof. The peripheral device 250 may also include a power source, such as a battery. The peripheral device 250 may not necessarily include all of the components shown in FIG. 2. The user interface 252 may, for example, include a touch-screen interface, a microphone (e.g., to receive voice commands), or a speaker, a vibration circuit, or any combination thereof, which may receive information from a user (e.g., glucose values) or deliver information to the user such as glucose values, glucose trends (e.g., an arrow, graph, or chart), or glucose alerts. The processor 256 may be configured to present information to a user, or receive input from a user, via the user interface 252. The processor 256 may also be configured to store and retrieve information, such as communication information (e.g., pairing information or data center access information), user information, sensor data or trends, or other information in the memory circuit 254. The wireless communication circuit 258 may include a transceiver and antenna configured to communicate via a wireless protocol, such as Bluetooth, MICS, or any of the other options described above. The sensor 260 may, for example, include an accelerometer, a temperature sensor, a location sensor, biometric sensor, or blood glucose sensor, blood pressure sensor, heart rate sensor, respiration sensor, or other physiologic sensor. The peripheral device 250 may, for example, be a hand-held smart device 112 (e.g., smartphone or other device such as a proprietary handheld device available from Dexcom), tablet 114, smart pen 116, watch or other wearable device 120, or computer 118 shown in FIG. 1.

The peripheral device 250 may be configured to receive and display sensor information that may be transmitted by sensor electronics 106 (e.g., in a customized data package that is transmitted to the display devices based on their respective preferences). Sensor information (e.g., blood glucose concentration level) or an alert or notification (e.g., "high glucose level", "low glucose level" or "fall rate alert" may be communicated via the user interface 252 (e.g., via visual display, sound, or vibration). In some examples, the peripheral device 250 may be configured to display or otherwise communicate the sensor information as it is communicated from the sensor electronics 106 (e.g., in a data package that is transmitted to respective display devices). For example, the peripheral device 250 may transmit data that has been processed (e.g., an estimated analyte concentration level that may be determined by processing raw sensor data), so that a device that receives the data may not be required to further process the data to determine usable information (such as the estimated analyte concentration level). In other examples, the peripheral device 250 may process or interpret the received information (e.g., to declare an alert based on glucose values or a glucose trend). In various examples, the peripheral device 250 may receive information directly from sensor electronics 106, or over a network (e.g., via a cellular or Wi-Fi network that receives information from the sensor electronics 106 or from a device that is communicatively coupled to the sensor electronics 106).

Referring again to FIG. 2, the medical device 270 may include a user interface 272, a memory circuit 274, a processor 276, a wireless communication circuit 278, a sensor 280, a therapy circuit 282, or any combination thereof. The user interface 272 may, for example, include a touch-screen interface, a microphone, or a speaker, a vibration circuit, or any combination thereof, which may receive information from a user (e.g., glucose values, alert preferences, calibration coding) or deliver information to the user, such as e.g., glucose values, glucose trends (e.g., an arrow, graph, or chart), or glucose alerts. The processor 276 may be configured to present information to a user, or receive input from a user, via the user interface 272. The processor 276 may also be configured to store and retrieve information, such as communication information (e.g., pairing information or data center access information), user information, sensor data or trends, or other information in the memory circuit 274. The wireless communication circuit 278 may include a transceiver and antenna configured communicate via a wireless protocol, such as Bluetooth, Medical Implant Communication System (MICS), Wi-Fi, Zigbee, or a cellular protocol (e.g., CDMA (Code Division Multiple Access) or GSM (Global System for Mobiles)). The sensor 280 may, for example, include an accelerometer, a temperature sensor, a location sensor, biometric sensor, or blood glucose sensor, blood pressure sensor, heart rate sensor, respiration sensor, or other physiologic sensor. The medical device 270 may include two or more sensors (or memories or other components), even though only one sensor 280 is shown in the example in FIG. 2. In various examples, the medical device 270 may be a smart handheld glucose sensor (e.g., blood glucose meter), drug pump (e.g., insulin pump), or other physiologic sensor device, therapy device, or combination thereof. In various examples, the medical device 270 may be the medical device 108, peripheral medical device 122, wearable device 120, wearable sensor 130, or wearable sensor 136 shown in FIG. 1.

In examples where the peripheral medical device 122 or medical device 270 is an insulin pump, the pump and analyte sensor system 102 may be in two-way communication (e.g., so the pump can request a change to an analyte transmission protocol, e.g., request a data point or request data on a more frequent schedule), or the pump and analyte sensor system 102 may communicate using one-way communication (e.g., the pump may receive analyte concentration level information from the analyte sensor system). In one-way communication, a glucose value may be incorporated in an advertisement message, which may be encrypted with a previously-shared key. In a two-way communication, a pump may request a value, which the analyte sensor system 102 may share, or obtain and share, in response to the request from the pump, and any or all of these communications may be encrypted using one or more previously-shared keys. An insulin pump may receive and track analyte (e.g., glucose) values transmitted from analyte sensor system 102 using one-way communication to the pump for one or more of a variety of reasons. For example, an insulin pump may suspend or activate insulin administration based on a glucose value being below or above a threshold value.

In some examples, the system 100 shown in FIG. 1 may include two or more peripheral devices that each receives information directly or indirectly from the analyte sensor system 102. Because different display devices provide many different user interfaces, the content of the data packages (e.g., amount, format, and/or type of data to be displayed, alarms, and the like) may be customized (e.g., programmed differently by the manufacturer and/or by an end user) for each particular device. For example, in the embodiment of FIG. 1, a plurality of different peripheral devices may be in direct wireless communication with a sensor electronics module (e.g., such as an on-skin sensor electronics 106 that is physically connected to the continuous analyte sensor 104) during a sensor session to enable a plurality of different types and/or levels of display and/or functionality associated with the displayable sensor information, or, to save battery power in the sensor system 102, one or more specified devices may communicate with the analyte sensor system 102 and relay (i.e., share) information to other devices directly or through a server system (e.g., a network-connected data center) 126.

FIG. 3A is a side view of an analyte sensor system, illustrating an analyte sensor 34 implanted into a host. A mounting unit 14 may be adhered to the host's skin using an adhesive pad 8. The adhesive pad 8 may be formed from an extensible material, which may be removably attached to the skin using an adhesive. The sensor electronics 106 may mechanically couple to the adhesive pad 8.

Figure 3B:
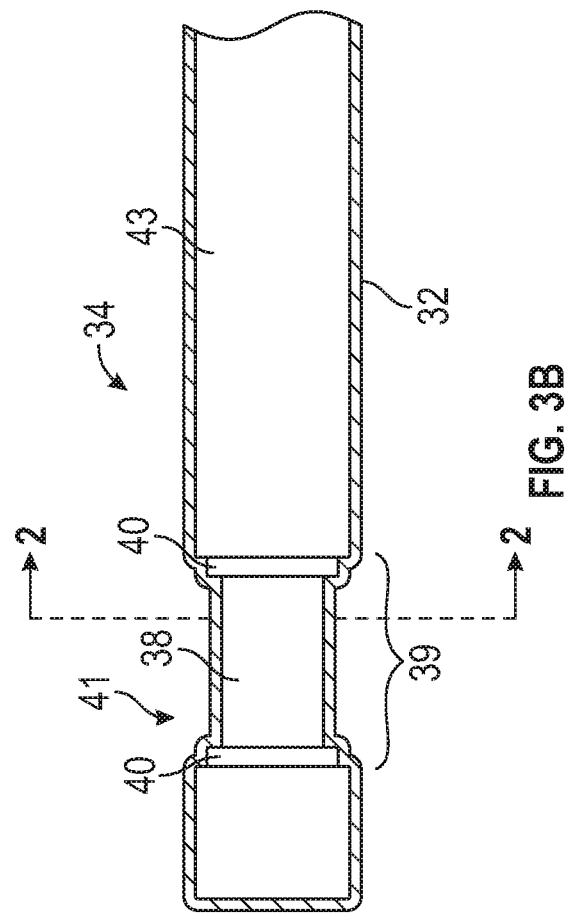
FIG. 3B is an enlarged view of an example analyte sensor portion of the analyte sensor system shown in FIG. 3A.

FIG. 3B is an enlarged view of a distal portion of the analyte sensor 34. The analyte sensor 34 may be adapted for insertion under the host's skin and may be mechanically coupled to the mounting unit 14 and electrically coupled to the sensor electronics 106. The example analyte sensor 34 shown in FIG. 3B includes an elongated conductive body 41. The elongated conductive body 41 can include a core with various layers positioned thereon. A first layer 38 that at least partially surrounds the core and includes a working electrode, for example located in window 39). In some examples, the core and the first layer 38 are made of a single material (such as, for example, platinum). In some examples, the elongated conductive body 41 is a composite of two conductive materials, or a composite of at least one conductive material and at least one non-conductive material. A membrane system 32 is located over the working electrode and may cover other layers and/or electrodes of the sensor 34, as described herein.

The first layer 38 may be formed of a conductive material. The working electrode (at window 39) is an exposed portion of the surface of the first layer 38. Accordingly, the first layer 38 is formed of a material configured to provide a suitable electroactive surface for the working electrode. Examples of suitable materials include, but are not limited to, platinum, platinum-iridium, gold, palladium, iridium, graphite, carbon, a conductive polymer, an alloy, and/or the like.

A second layer 40 surrounds at least a portion of the first layer 38, thereby defining boundaries of the working electrode. In some examples, the second layer 40 serves as an insulator and is formed of an insulating material, such as polyimide, polyurethane, parylene, or any other suitable insulating materials or materials. In some examples, the second layer 40 is configured such that the working electrode (of the layer 38) is exposed via the window 39.

In some examples, the sensor 34 further includes a third layer 43 comprising a conductive material. The third layer 43 may comprise a reference electrode. In some examples, the third layer 43, including the reference electrode, is formed of a silver-containing material that is applied onto the second layer 40 (e.g., an insulator). The silver-containing material may include various materials and be in various forms such as, for example, Ag/AgCl-polymer pasts, paints, polymer-based conducting mixtures, inks, etc.

The analyte sensor 34 may include two (or more) electrodes, e.g., a working electrode at the layer 38 and exposed at window 39 and at least one additional electrode, such as a reference electrode of the layer 43. In the example arrangement of FIG. 1B, the reference electrode also functions as a counter electrode, although other arrangements can include a separate counter electrode. While the analyte sensor 34 may be used with a mounting unit in some examples, in other examples, the analyte sensor 34 may be used with other types of sensor systems. For example, the analyte sensor 34 may be part of a system that includes a battery and sensor in a single package, and may optionally include, for example, a near-field communication (NFC) circuit.

FIG. 3C is a cross-sectional view through the sensor 34 of FIG. 3B on plane 2-2 illustrating a membrane system 32. The membrane system 32 may include a number of domains (e.g., layers). In an example, the membrane system 32 may include an enzyme domain 42, a diffusion resistance domain 44, and a bioprotective domain 46 located around the working electrode. In some examples, a unitary diffusion resistance domain and bioprotective domain may be included in the membrane system 32 (e.g., wherein the functionality of both the diffusion resistance domain and bioprotective domain are incorporated into one domain).

The membrane system 32, in some examples, also includes an electrode layer 47. The electrode layer 47 may be arranged to provide an environment between the surfaces of the working electrode and the reference electrode that facilitates the electrochemical reaction between the electrodes. For example, the electrode layer 47 may include a coating that maintains a layer of water at the electrochemically reactive surfaces of the sensor 34.

In some examples, the sensor 34 may be configured for short-term implantation (e.g., from about 1 to 30 days). However, it is understood that the membrane system 32 can be modified for use in other devices, for example, by including only one or more of the domains, or additional domains. For example, a membrane system may include a plurality of resistance layers, or a plurality of enzyme layers. In some example, the resistance domain 44 may include a plurality of resistance layers, or the enzyme domain 42 may include a plurality of enzyme layers.

The diffusion resistance domain 44 may include a semi-permeable membrane that controls the flux of oxygen and glucose to the underlying enzyme domain 42. As a result, the upper limit of linearity of glucose measurement is extended to a much higher value than that which is achieved without the diffusion resistance domain 44.

In some examples, the membrane system 32 may include a bioprotective domain 46, also referred to as a domain or biointerface domain, comprising a base polymer as described in more detail elsewhere herein. However, the membrane system 32 of some examples can also include a plurality of domains or layers including, for example, an electrode domain, an interference domain, or a cell disruptive domain, such as described in more detail elsewhere herein and in U.S. Pat. Nos. 7,494,465, 8,682,408, and 9,044,199, which are incorporated herein by reference in their entirety.

It is to be understood that sensing membranes modified for other sensors, for example, may include fewer or additional layers. For example, in some examples, the membrane system 32 may comprise one electrode layer, one enzyme layer, and two bioprotective layers, but in other examples, the membrane system 32 may comprise one electrode layer, two enzyme layers, and one bioprotective layer. In some examples, the bioprotective layer may be configured to function as the diffusion resistance domain 44 and control the flux of the analyte (e.g., glucose) to the underlying membrane layers.

In some examples, one or more domains of the sensing membranes may be formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones and block copolymers thereof including, for example, di-block, tri-block, alternating, random and graft copolymers.

In some examples, the sensing membrane can be deposited on the electroactive surfaces of the electrode material using known thin or thick film techniques (for example, spraying, electro-depositing, dipping, or the like). The sensing membrane located over the working electrode does not have to have the same structure as the sensing membrane located over the reference electrode 30; for example, the enzyme domain 42 deposited over the working electrode does not necessarily need to be deposited over the reference or counter electrodes.

Although the examples illustrated in FIGS. 3B-3C involve circumferentially extending membrane systems, the membranes described herein may be applied to any planar or non-planar surface, for example, the substrate-based sensor structure of U.S. Pat. No. 6,565,509 to Say et al., which is incorporated by reference.

In an example in which the analyte sensor 34 is a glucose sensor, glucose analyte can be detected utilizing glucose oxidase, which produces hydrogen peroxide ($H_2O_2$) as a byproduct of the reaction of glucose with glucose oxidase. The hydrogen peroxide reacts with the surface of the working electrode, producing two protons ($2H^+$), two electrons ($2e^-$) and one molecule of oxygen ($O_2$), which produces an electronic current that may be detected by the sensor electronics 106. The amount of current is a function of the glucose concentration level. A calibration curve may be used to provide an estimated glucose concentration level based on a measured current. The amount of current is also a function of the diffusivity of glucose through the sensor membrane. The glucose diffusivity may change over time, which may cause the sensor glucose sensitivity to change over time, or "drift."

Figure 4:
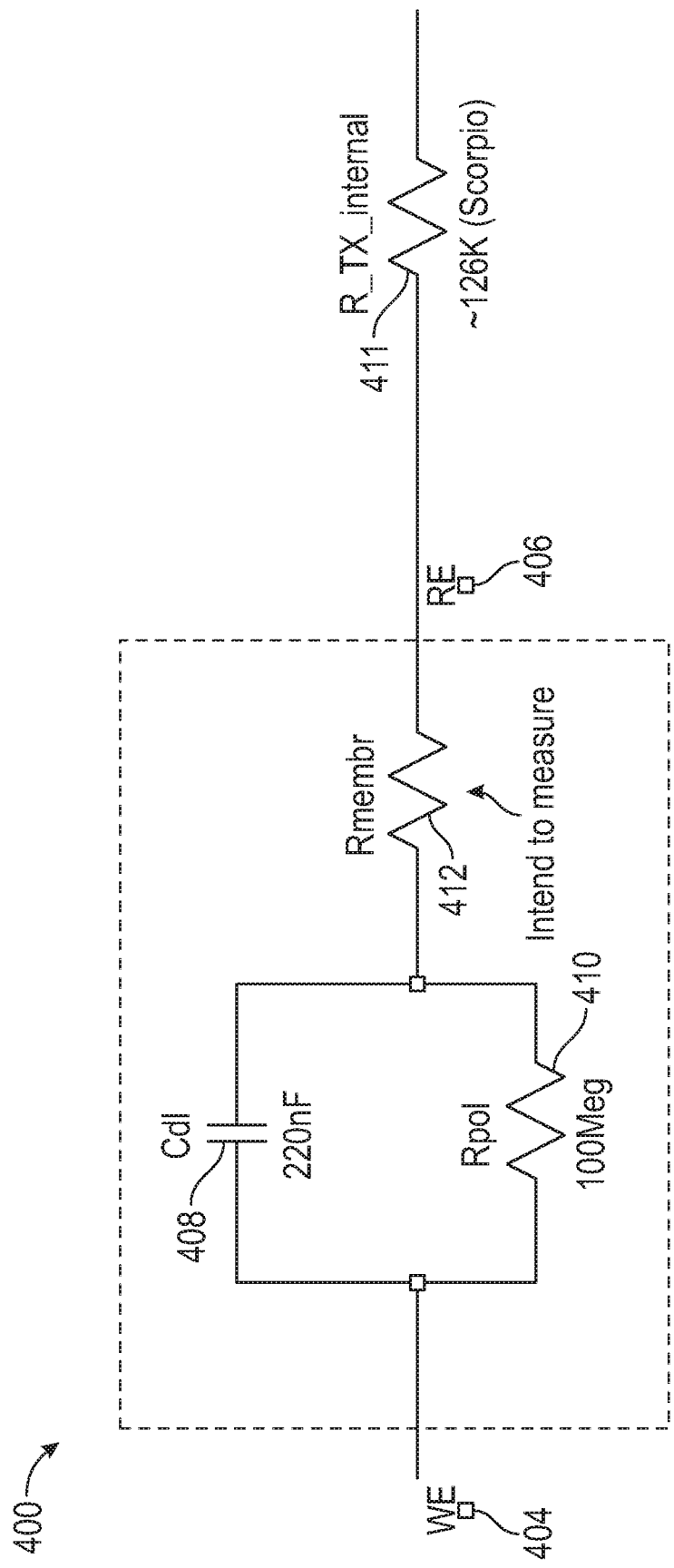
FIG. 4 is a schematic illustration of a circuit that represents the behavior of an analyte sensor.

FIG. 4 is a schematic illustration of a circuit 400 that represents the behavior of an analyte sensor, such as the sensor 34 shown in FIGS. 3A-3C. As described above, the interaction of hydrogen peroxide (generated from the interaction between glucose analyte and glucose oxidase) and working electrode (WE) 404 produces a voltage differential between the working electrode (WE) 404 and reference electrode (RE) 406, which drives a current that may be measured by sensor electronics 106 and used to estimate a glucose concentration level. The circuit 400 also includes a double-layer capacitance (Cdl) 408, which occurs at an interface between the working electrode (WE) 404 and the adjacent membrane (not shown, see description above).

In a typical in vivo analyte sensor, a double-layer capacitance (Cdl) may occur at the interface between the working electrode 404 and the adjacent membrane due to the presence (e.g., during application of an applied voltage between the working electrode 404 and reference electrode) of two layers of ions with opposing polarity. The equivalent circuit 400 may also include a polarization resistance (Rpol) 410, which may be relatively large, and may be modeled, for example, as a static value (e.g., 100 mega-Ohms), or as a variable quantity that varies as a function of glucose concentration level.

An estimated analyte concentration level may be determined based upon A) a measured current (charge) flow through the analyte sensor membrane 412 when a voltage is applied to the sensor circuit and B) a glucose sensitivity of the sensor, which correlates a detected current flow to a glucose concentration level.

The change in glucose diffusivity over time presents a problem, in that two unknown variables (glucose concentration around the membrane 412 and glucose diffusivity in the membrane 412) are present in the system. For example, frequent blood glucose meter calibrations may be used to account for the drift, but this need for meter calibrations may be undesirable for a variety of reasons (e.g., inconvenience to the patient, cost, the potential for inaccurate blood glucose meter data, etc.).

With reference to the equivalent circuit 400, when a voltage is applied across the working and reference electrodes 404 and 406, a current may be considered to flow (forward or backward depending on polarity) through the internal electronics of transmitter (represented by R_Tx_internal) 411; through the reference electrode (RE) 406 and working electrode (WE) 404, which may be designed to have a relatively low resistance; and through the sensor membrane 412 (Rmembr, which is relatively small). Depending on the state of the circuit, current may also flow through, or into, the relatively large polarization resistance 410 (which is indicated as a fixed resistance, but may also be a variable resistance that varies with the body's glucose level, where a higher glucose level provides a smaller polarization resistance), or into the double-layer capacitance 408 (i.e., to charge the double-layer membrane capacitor formed at the working electrode 404), or both.

The impedance (or conductance) of the membrane (Rmembr) 412 is related to electrolyte mobility in the membrane, which is in turn related to glucose diffusivity in the membrane. As the impedance goes down (i.e., conductance goes up, as electrolyte mobility in the membrane 412 goes up), the glucose sensitivity goes up (i.e., a higher glucose sensitivity means that a particular glucose concentration will produce a larger signal in the form of more current or charge flow). Impedance, glucose diffusivity, and glucose sensitivity are further described in U.S. Patent Publication No. US2012/0262298, which is incorporated by reference in its entirety.

Determination of Impedance by Measuring Current or Charge Count.

The relationship between impedance (or conductance) of an analyte sensor circuit and analyte diffusivity (e.g., glucose diffusivity) may allow for determination of an accurate glucose sensitivity based upon a determined impedance value of the sensor circuit. In a situation (e.g., in vivo implantation) where the sensor sensitivity is not precisely known, but impedance can be determined from measurements (e.g., using Ohm's law), a predicted sensitivity may be determined based on a correlation between impedance (or conductivity) and glucose sensitivity.

Figure 5A:
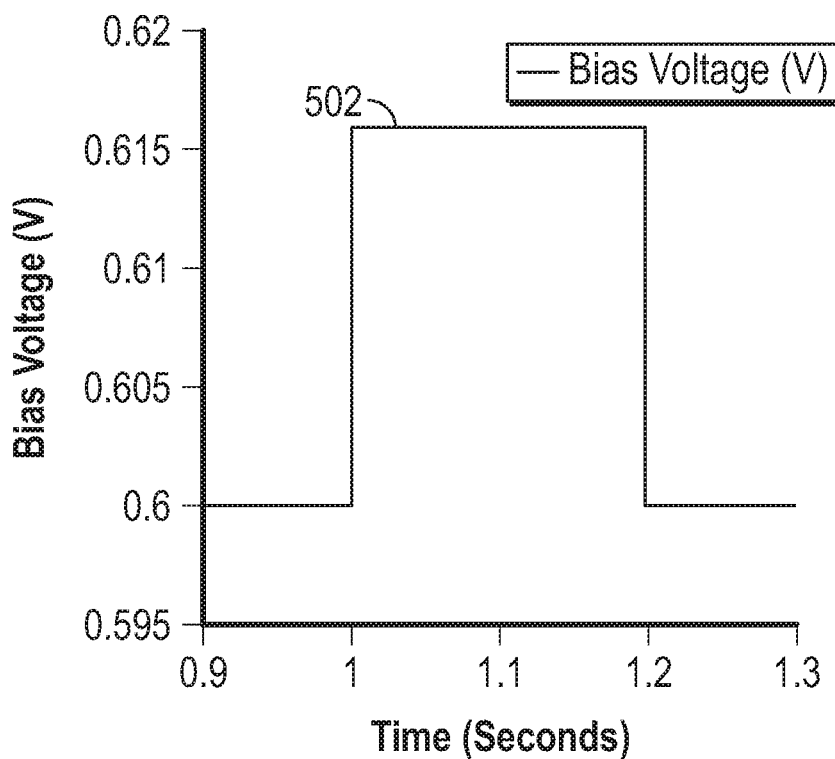
FIG. 5A is a graph that shows a bias voltage step.
Figure 5B:
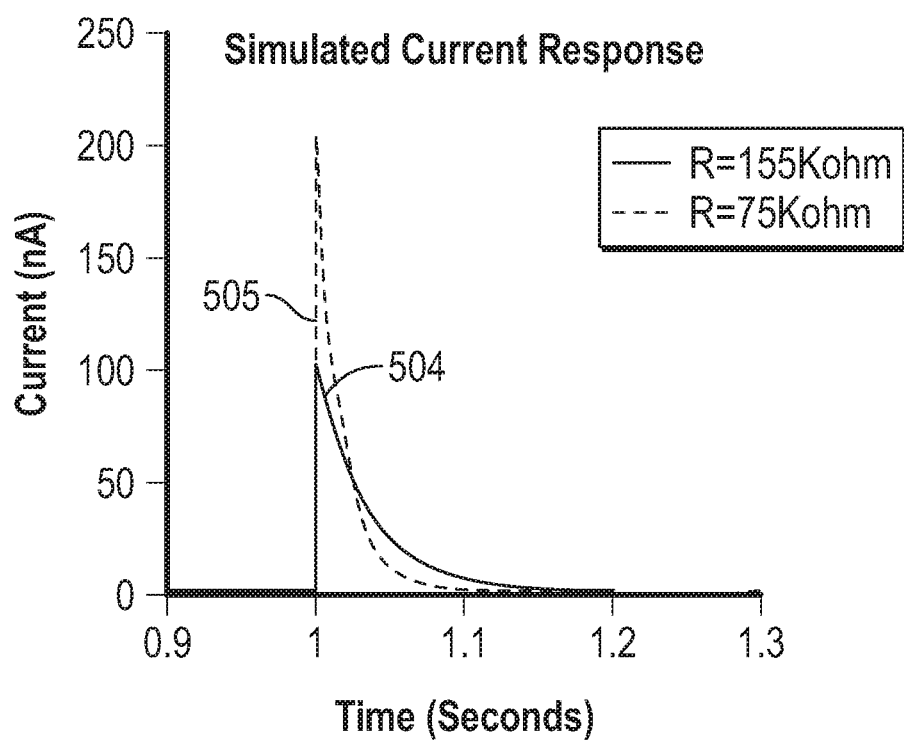
FIG. 5B is a graph that shows a simulated current response to the voltage step shown in FIG. 5A.

In some examples, impedance may be determined based upon application of a known voltage (or voltage step) and measurement of current flow (e.g., integrating charge count over time). In a typical analyte sensor, a sensor bias voltage is applied to a sensor circuit to enable accurate sensing using a sense amplifier. FIG. 5A is a chart that shows a bias voltage 502 stepped up from 0.600 Volts to 0.616 Volts. FIG. 5B shows the corresponding simulated response 504, 505 for a circuit having a 155 kiloohm impedance and a circuit having a 75 kiloohm impedance. As shown in FIG. 5B, the current for the 75 kiloohm circuit rises to a peak current value of over 200 nanoamps, and the response current for the 155 kiloohm circuit rises to about 100 nanoamps. The response current for both circuits then decays as the double-layer capacitance adjusts to the change in applied bias (e.g., as the Cdl in FIG. 4 charges). It should be noted that both FIGS. 5A and 5B illustrate the change in sensor current in response to the transient voltage step. Accordingly, what is shown is the incremental delta current riding on top of an already-existing non-zero glucose current under 0.6V bias.

In a sensor system, a circuit with 155 kiloohm impedance may be differentiated from a circuit with 75 kiloohm impedance based on the magnitude of the current response. In some examples, the impedance may be determined based on the current response, and the resistance attributable to the membrane (Rmembr 412 in FIG. 4) may be determined based upon knowledge (or estimates) of the other impedances in the circuit (e.g., R_TX_internal may be estimated) and Kirchoff's law.

Figure 5C:
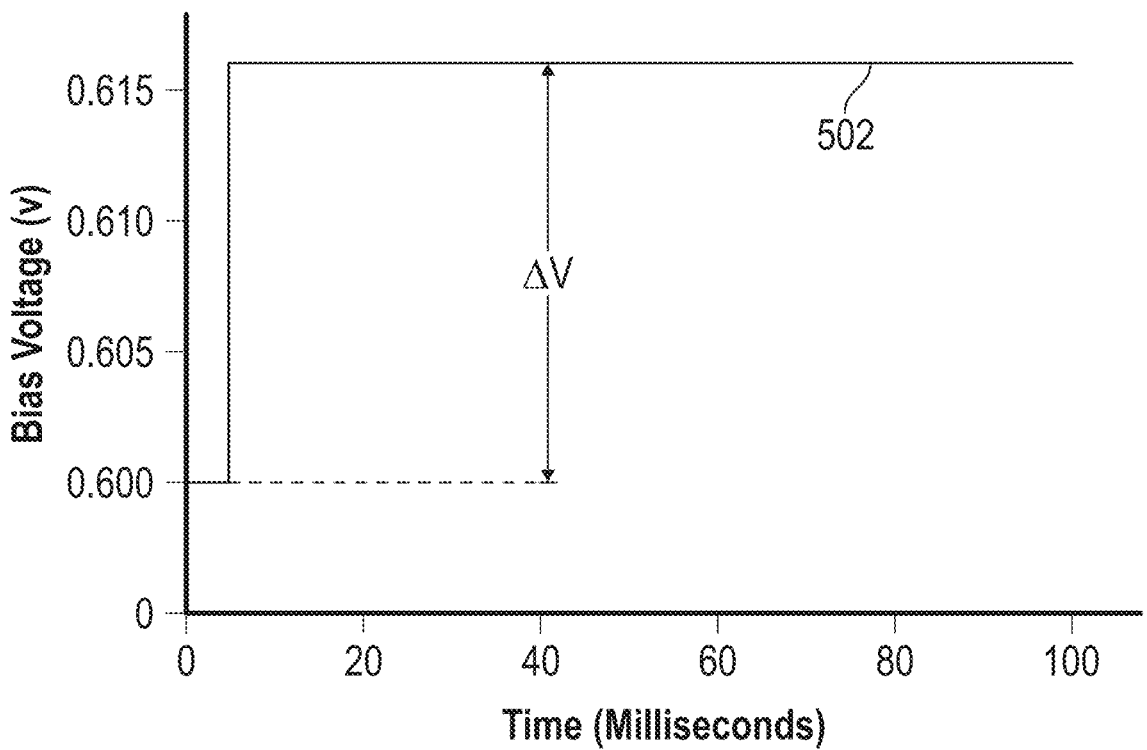
FIG. 5C is a graph that shows the voltage step of FIG. 5A with a time axis in milliseconds.
Figure 5D:
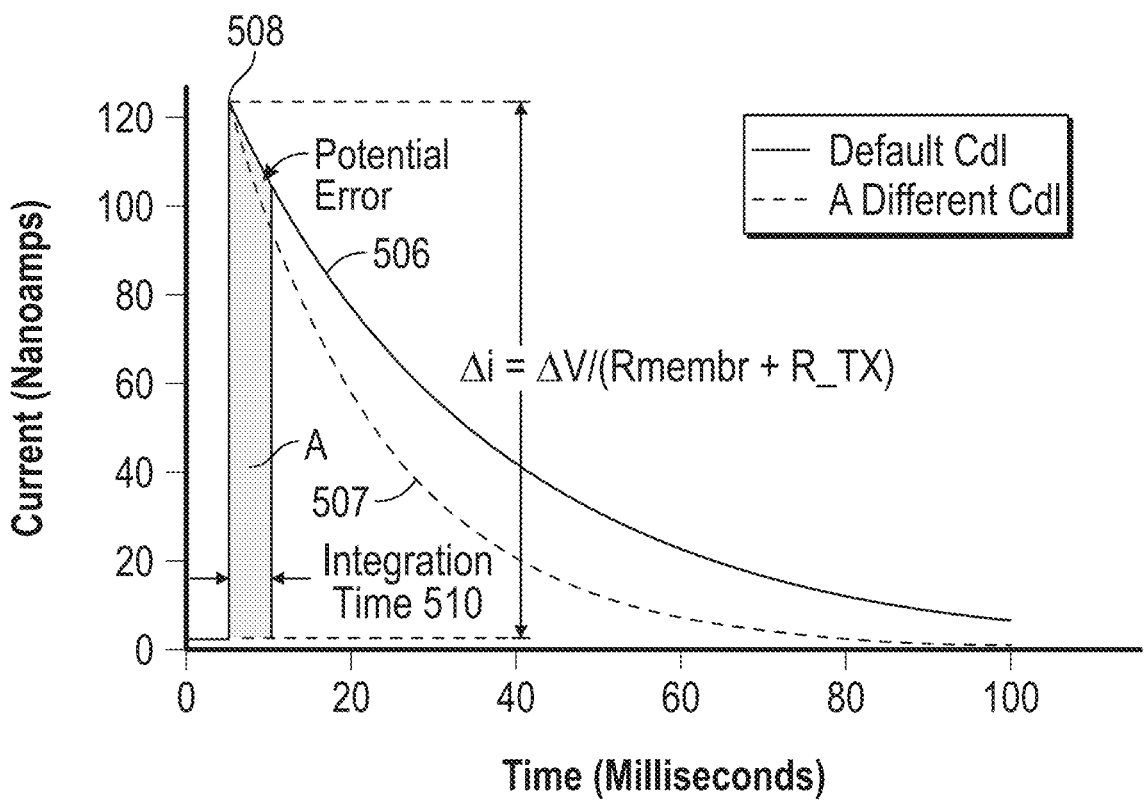
FIG. 5D is a graph that shows the current response to the step of FIG. 5C, with a time axis in milliseconds.

FIG. 5C is a chart that shows a bias voltage 502 stepped up from 0.600 Volts to 0.616 Volts. FIG. 5D shows the current response 506 to the step-up in voltage plotted against time in milliseconds. As shown in FIG. 5D, the sensed current quickly rises to a peak current value 508 (e.g., 120 nA), and then decays as the double-layer capacitance adjusts to the change in applied bias (e.g., as the Cdl 408 in FIG. 4 charges). FIG. 5D also shows a response current 507 for a second sensor with a different double-layer capacitance value, which is described below.

In an analyte sensor, the peak current value 508 may not be measurable directly, but it may be determined by measuring the accumulated charge over an Integration Time 510 (which may, for example, be e.g., 3.9 ms, or a value between 3-5 ms, or a value between 2 and 20 ms, or a value between 2 and 40 ms) after the step-up of the bias voltage, which is the equivalent of integrating under the current response curve for the area A indicated in FIG. 5D.

Simply dividing the integrated current by the specified period of time yields an average current over the integration time, which may be used as an approximation of the peak current, but this approximation is less than the actual peak due to the current decay caused by the double-layer capacitance. A more accurate determination of the peak current may be obtained by assuming a value (e.g., an experimentally determined value) for the double-layer capacitance (Cdl), which allows for derivation of a peak value based upon the integrated current (PI) and the assumed value for Cdl.

Because the capacitance of the membrane (not shown in FIG. 4) may be much smaller than the double-layer capacitance (Cdl), the polarization resistance (Rpol) may be very high (>1 megaOhm), and the capacitive resistance of the membrane is initially very large after the voltage step, substantially all of the current flows through Rmembr 412 and Cdl 408. In a short period (e.g., 5 ms) after the voltage step, the total sensor resistance may be estimated as the membrane resistance (Rmembr 412). The membrane resistance (Rmembr 412) may thus be estimated using Ohm's law: $\Delta i = \Delta V/(Rmembr + R\_TX)$. After the peak current is determined (e.g., based up integrated charge for a short period after the voltage step), this equation may be solved for the resistance of the membrane (Rmembr 412).

An estimate of the integrated pulse current may be obtained by integrating over a small portion of the current decay curve, as shown for example, in FIG. 5D. An integration over a short integration time after the voltage step may be used to estimate peak current. The integration time may be relatively short compared to the time it takes the current response to a step voltage to decay (i.e., compared to the capacitor charge time for the double-layer capacitor after application of the step in bias voltage). For example, an integration time of four milliseconds (4 ms) may be used to estimate peak current. Other important parameters may include the rise time of the voltage step (or bias pulse), the impedance of sensor electronics (which may be measured and consistently controlled in manufacturing), the pulse potential (e.g., a 16 mV step may be applied), and alignment of the current integration with the rising edge of the voltage step (which may be controlled by a clock in the sensor electronics, e.g., the start of the current integration may be one clock cycle after the beginning of a voltage step), and duty cycle (e.g., a five percent duty cycle may be used to allow a sensor membrane capacitance to discharge to a consistent pre-pulse state). In some examples, a voltage step may be applied before each glucose measurement, or recurrently (e.g., before every second glucose measurement, or every third, fourth, or fifth glucose measurement, or once an hour, or once or twice or more times per day).

FIG. 5E shows integrated pulse current 512, 514, 516 plotted against impedance for three different integration times (10 milliseconds, 25 milliseconds, and 125 milliseconds). For the 125 millisecond integration time, the integrated pulse current is approximately the same for three different impedance values (75 kOhm, 110 kOhm, 155 kOhm). Because the current is averaged over all or most of the current decay curve (i.e., the current reaches or approaches zero (or a baseline current) within 125 ms), the sensor circuits with different impedances all result in an integrated pulse current of about 30 nanoamps. This approximate equivalence in integrated pulse current for the three different impedance values would prevent determination of an accurate impedance estimate from the integrated pulse currents. In contrast, an integration time of 25 milliseconds results in different values of integrated pulse current for the three different impedance values. As a result, a sensor that integrates over a 25 millisecond integration time would allow for differentiation between sensor circuits having 75 kOhm, 110 kOhm, 155 kOhm impedance values or estimation of an impedance based on integrated pulse current. Using a 10 millisecond integration time provides even greater variation in integrated pulse current for different impedance values, which would improve performance in determining an impedance estimate.

While the description above in some instances discloses absolute current and absolute voltage, it is understood that the methods may also be used with respect to a change in current ($\Delta i$), change in voltage ($\Delta V$), or change in impedance ($\Delta R$). For example, in some analyte sensors, the baseline current may not be zero, because of the presence of a steady bias voltage.

Figure 5F:
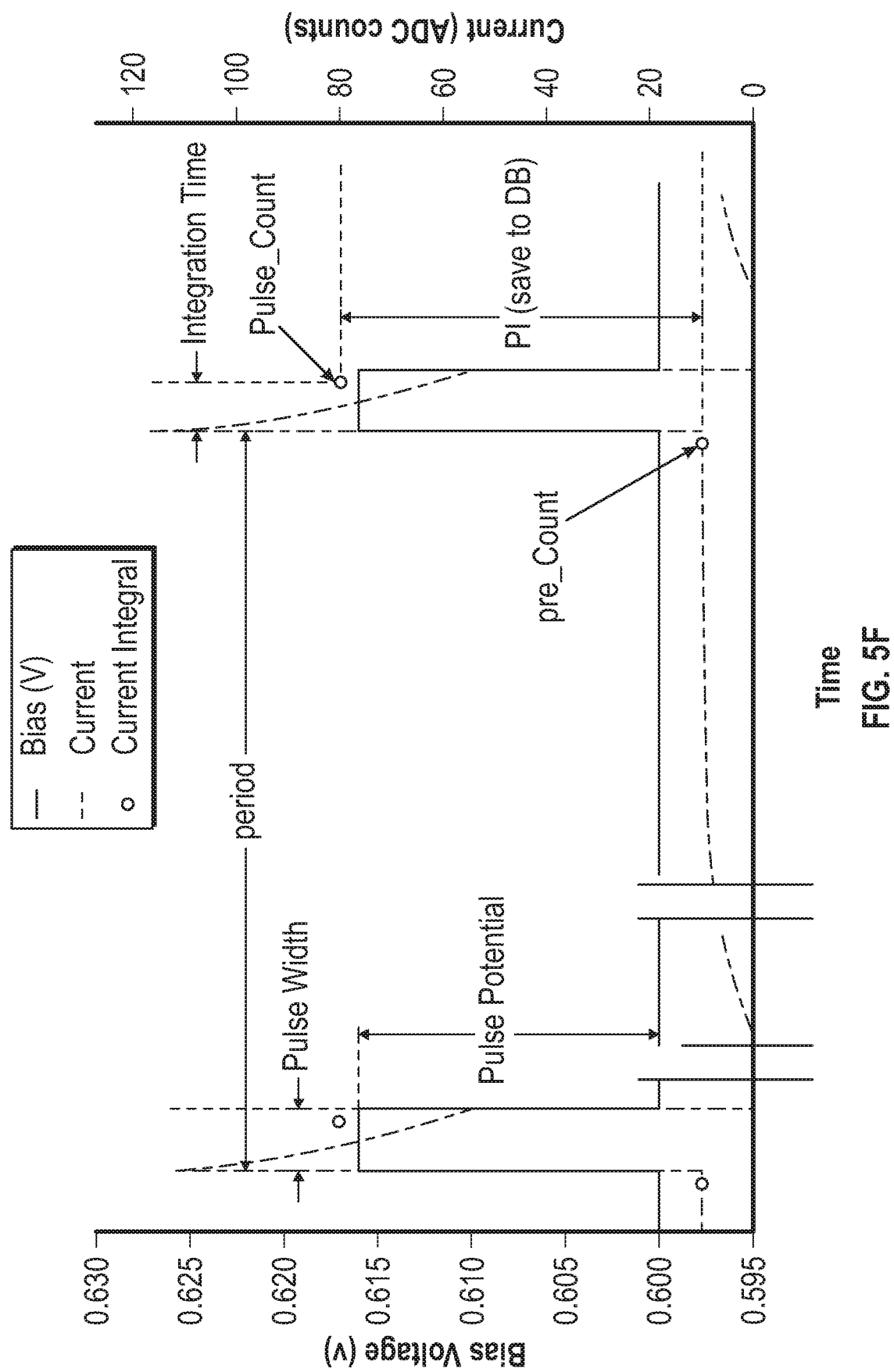
FIG. 5F is a graph that shows bias voltage overlaid onto the current response to a voltage step.

In some examples, a step voltage may be recurrently (e.g., periodically) applied to a sensor circuit. The step voltage may be maintained for a period that is as long or longer than the entire current decay curve, as shown in FIG. 5C, or the step voltage may be returned to a baseline value before the current has decayed to a steady state value, as shown in FIG. 5F. FIG. 5F shows bias voltage overlaid onto the current response to a voltage step ("Pulse Potential"). The step voltage step (e.g., increased from 0.600 Volts to 0.616) may be applied and maintained for a segment of time (Integration Time), and the bias voltage may then be returned to the level it was at prior to the step (e.g., returned to 0.600 Volts). A Current Integral for the Integration Time may be determined based on a difference in a charge count (e.g., obtained using a Coulomb counter) between a count value (Pulse_Count) at the end of the Integration Time and a count value (Pre_Count) at the beginning of the Integration Time. The Current Integral amounts to an accumulated charge for the pulse (PI), which may be stored in a database (DB) for comparison with past or future impedance values or may be used in a compensation algorithm to provide a more accurate estimated analyte concentration value.

When the bias voltage returns to its normal baseline level (e.g., when the Integration Time period expires and the bias voltage drops from 0.616 Volts back to 0.600 Volts), the capacitor begins to discharge (to move back to a 0.6 Volt charge state), and the observed current drops below the baseline value (because the capacitor is supplying some of the potential to maintain the bias voltage). Eventually, the current transitions back to its baseline (steady state) value.

After a period of time has expired, a second voltage step may be applied, and a second PI value may be determined in the manner described above.

Averaging of Charge Count Values Over Multiple Sampling Periods.

Figure 6A:
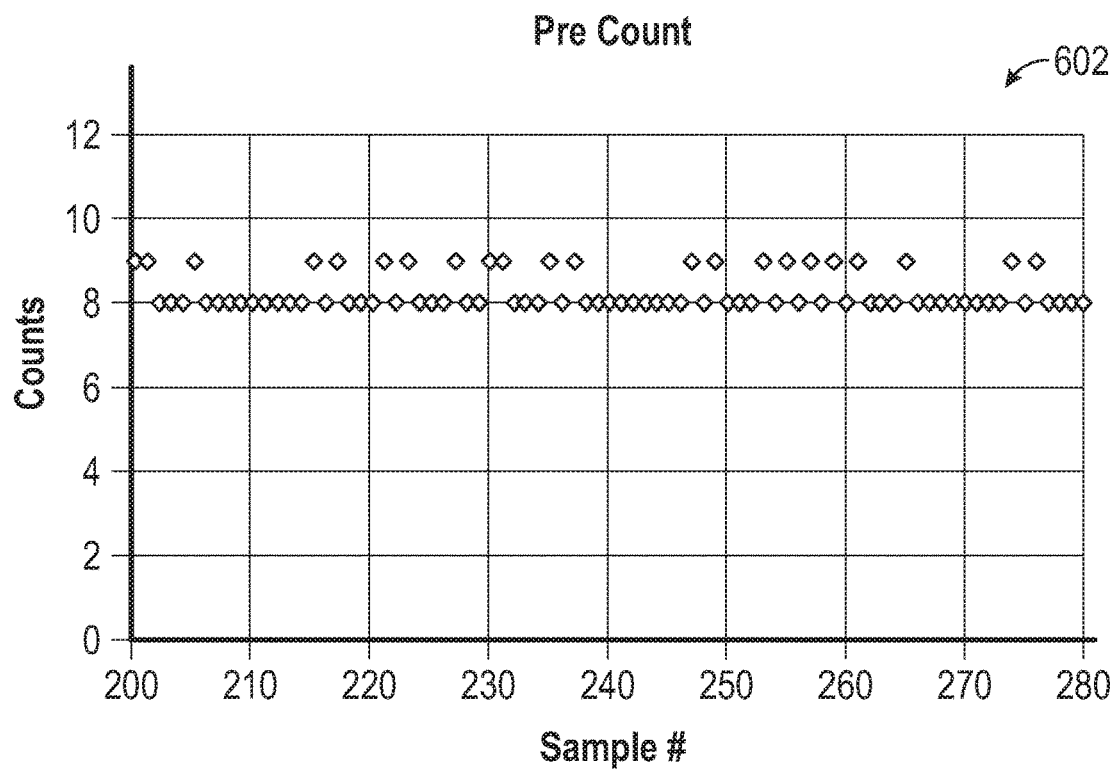
FIG. 6A is a graph that shows count values at the beginning of the Integration Time (Pre_Count) and at the end of the Integration Time (Pulse_Count) for a plurality of samples by a sensor.
Figure 6B:
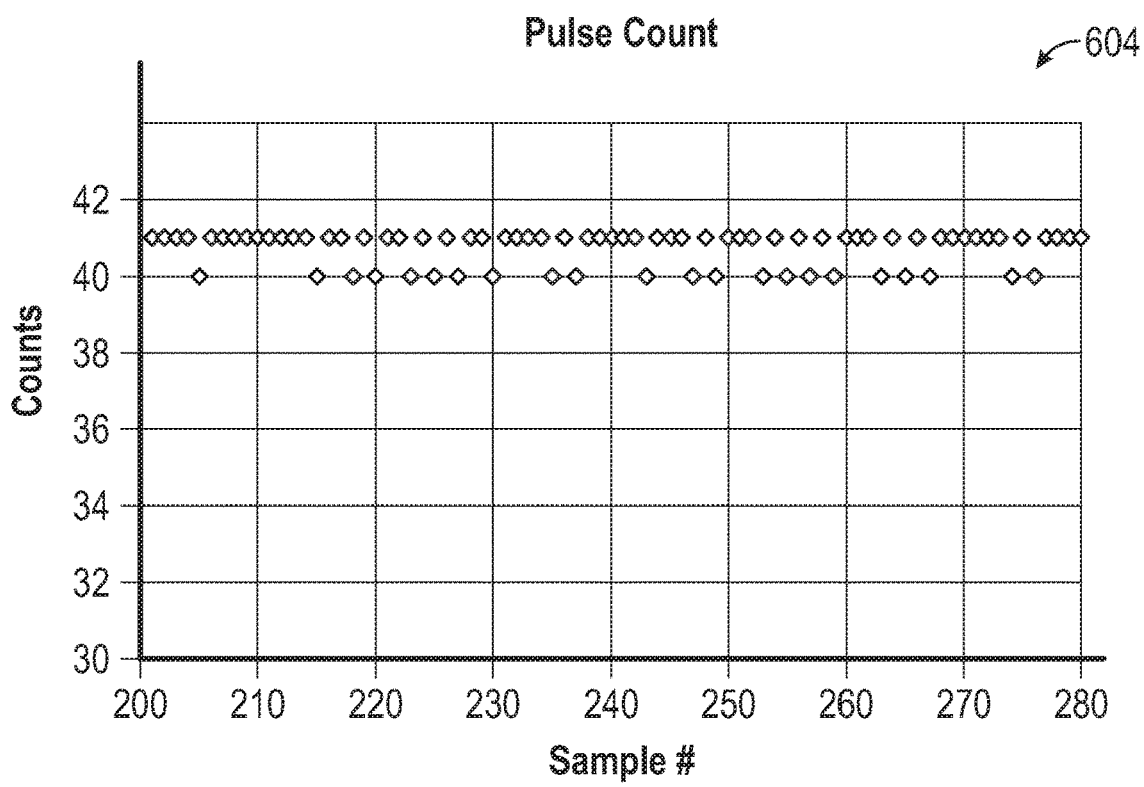
FIG. 6B is a graph that shows count values at the beginning of the Integration Time (Pre_Count) and at the end of the Integration Time (Pulse_Count) for the plurality of sensor samples of FIG. 6A.
Figure 6C:
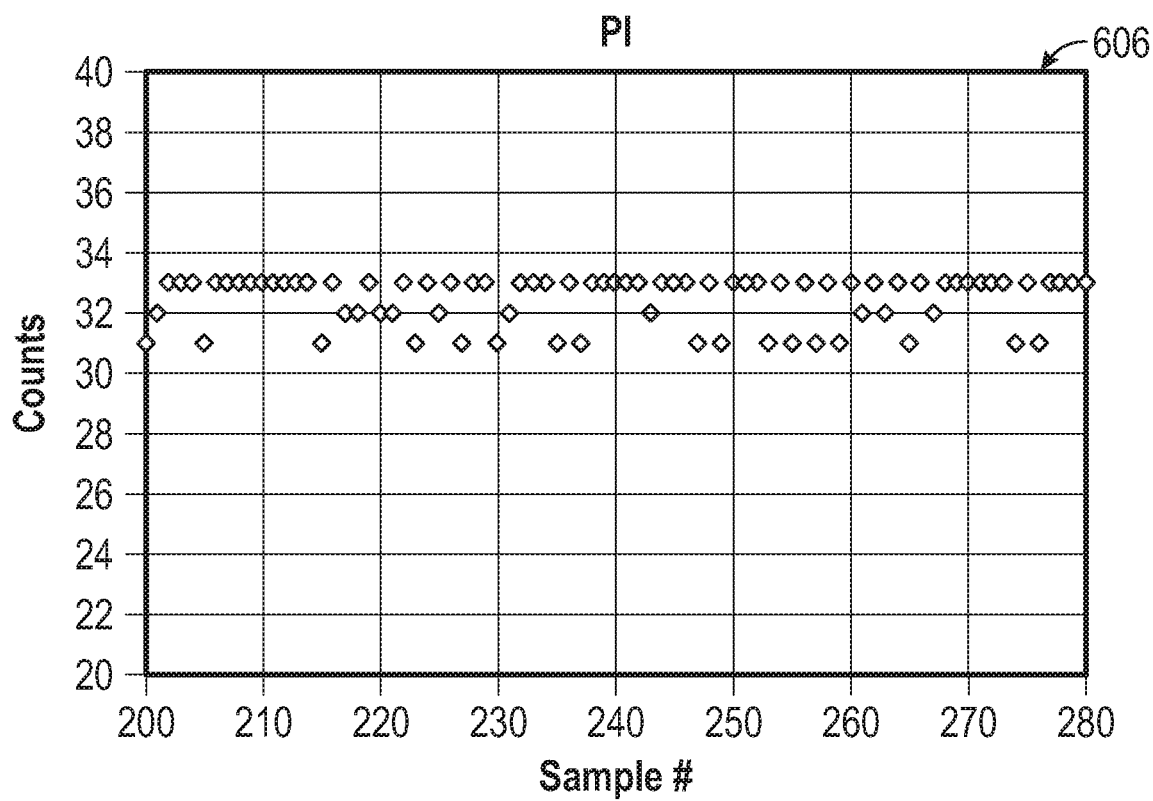
FIG. 6C is a graph that shows integrated charge count (PI) for the samples of FIGS. 6A and 6B.
Figure 6D:
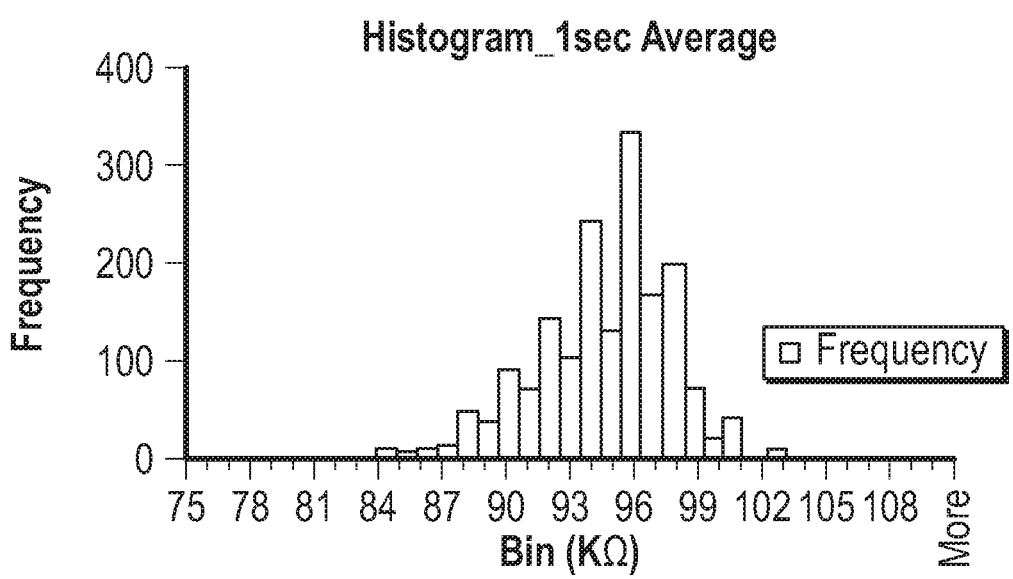
FIG. 6D is a histogram plot of determined impedance for a sensor, where charge count was averaged over a plurality of one-second sampling periods.
Figure 6E:
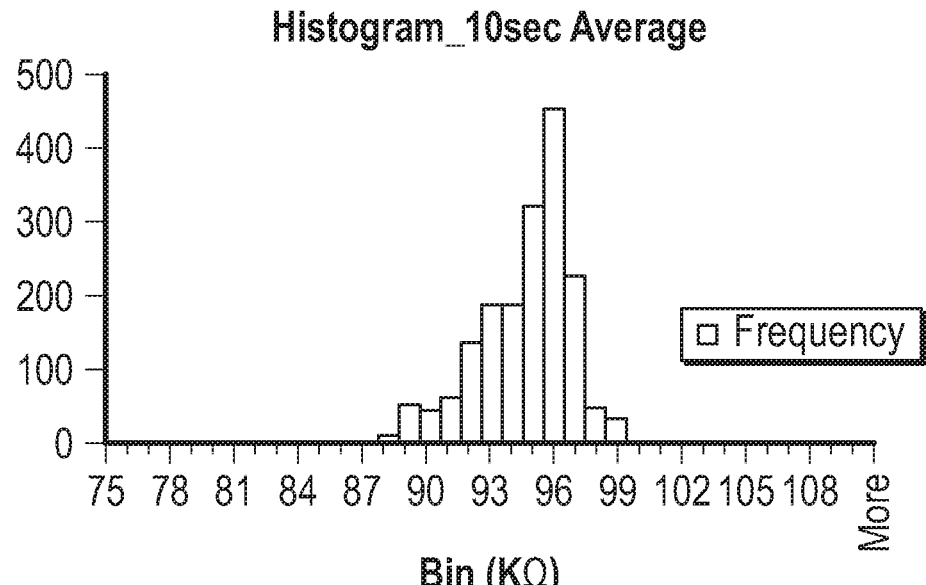
FIG. 6E is a histogram plot of determined impedance for a plurality of ten-second sampling periods.
Figure 6F:
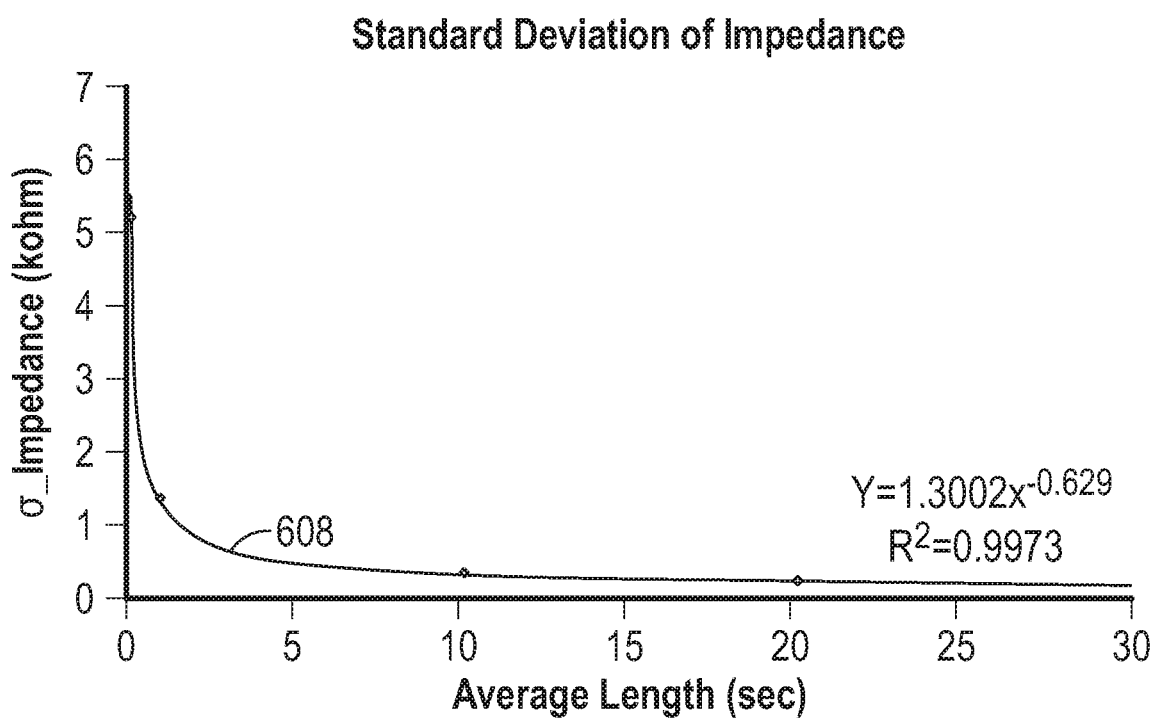
FIG. 6F is a graph that shows the standard deviation of determined impedance values for a sensor plotted against a length of time over which current (e.g., integrated charge count) was measured or determined.

FIGS. 6A and 6B show respective count values 602, 604 at the beginning of the Integration Time (Pre_Count) and at the end of the Integration Time (Pulse_Count) for a plurality of samples by a sensor. FIG. 6C shows the integrated charge count (PI) 606 for the Integration Time (Pulse_Count-Pre_Count.) The counts for multiple Integration Times in a sampling interval (e.g., 1 second, 10 seconds, 12 seconds, or 20 seconds) may be be averaged to determine an average (e.g., mean or median) integrated charge count (PI), which may increase the accuracy of the charge count (PI) or increase the accuracy of an impedance or sensitivity derived therefrom. FIG. 6D shows a histogram plot of determined impedance for a sensor, where charge count was averaged over a plurality of one-second sampling periods (e.g., at a rate of one sample every 5 milliseconds during the sampling period). FIG. 6E is a histogram plot of determined impedance for a plurality of ten-second sampling periods. The histogram based on ten-second sampling periods provides a tighter distribution (e.g., more clustering around 96 k$\Omega$ and a tighter standard deviation). While using an average value from a plurality of Integration Times may improve the accuracy of the integrated charge count (PI) and impedance or sensitivity derived therefrom, obtaining a large data set may have an adverse impact on battery life due to energy consumed in applying the voltage step and processing the resulting current. FIG. 6F shows the standard deviation of determined impedance values 608 for a sensor plotted against a length of time over which current (e.g., integrated charge count) was measured or determined. In some examples, an averaging time of about 1 second (e.g., 0.5 to 1.5 seconds, or 0.5 to 3 seconds) is used, to provide a set of determined impedance values having a standard deviation of less than 2 Ohms. In some examples, an averaging time of about 10 seconds or 12 seconds (e.g., 5 to 15 seconds, or 8 to 12 seconds, or 10 to 14 seconds) is used to collect current (e.g., integrated charge count) values, which may provide a set of determined impedance values with a standard deviation of less than 1 Ohm.

Pulsed Amperometric Response

Figure 7:
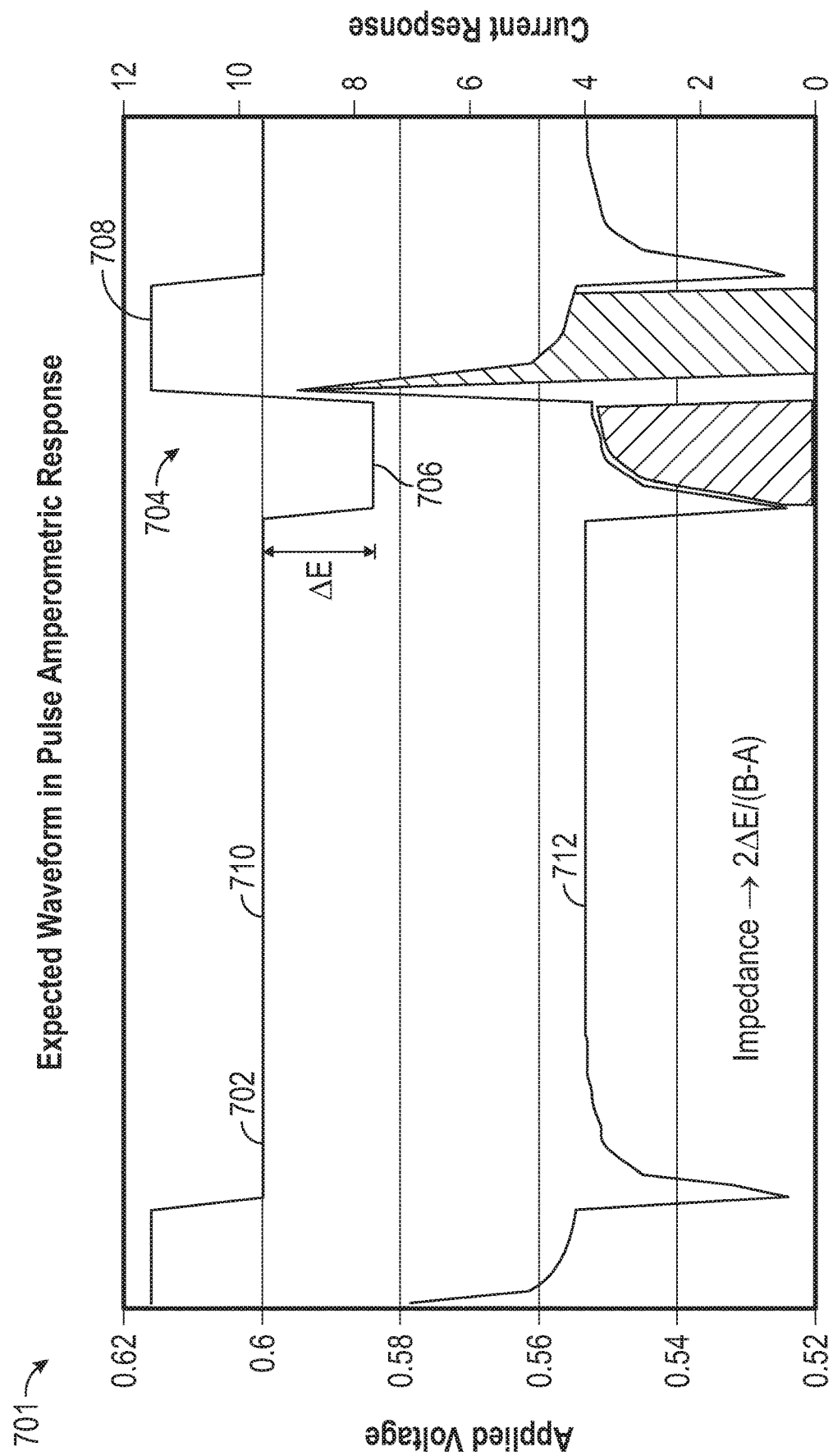
FIG. 7 is graph that shows an applied bias voltage with a biphasic pulse, plotted against time.

In some examples, an analyte sensor may apply a pulse instead of a voltage step. In some examples, the pulse may be a step pulse, as shown in FIG. 5E, in which, for example, a bias voltage is stepped up, and then eventually, after a relatively long period of time, the bias voltage is returned to a steady state value. In other examples, a pulse may be a biphasic pulse, as shown in FIG. 7. More complex pulse shapes are also possible.

FIG. 7 is a graph 701 that shows an applied bias voltage 702 with a biphasic pulse 704, plotted against time. While a square pulse shape is shown, other pulse shapes, such as a sine wave, are also possible. In the illustrated example, the bias voltage 702 has a baseline 710 that corresponds to a steady state (e.g., 0.6 Volts). In a first portion 706 of the pulse 704, the bias voltage 702 drops below the baseline 710 (e.g., from 0.6 Volts to 0.584 Volts) by an amount labeled ΔE, and then returns to the baseline 710. In a second portion 708 of the pulse 704, the bias voltage 702 rises (e.g., from 0.6 Volts to 0.616 Volts). The pulse 704 is illustrated as symmetric, i.e., in the first portion 706 the voltage 702 drops by value ΔE, and in the second portion 708 the voltage 702 rises by value ΔE, but other examples may use an asymmetric pulse.

The lower portion of the graph 701 shows the current response 712 in nanoamps. When the bias voltage 702 is dropped, the observed current response also drops (e.g., from 4 nanoamps to about 02 nanoamps). The observed current response then rises as the capacitor discharges a portion of its stored energy. In the example shown, the second portion 708 of the pulse 704 is timed to occur at (or around) the time the current response reaches a new steady state (e.g., slightly less than the original steady state, as determined by Ohm's law I=V/R). In other examples, the second portion of the pulse may occur sooner (i.e., the period of the pulse may be shorter than the illustrated example) or the second of the pulse may occur later (i.e., the period of the pulse may be longer).

The impedance may be determined from the change in voltage and the change in current in response to the voltage change. For example, for the pulse shown (with equal size pulses), the membrane impedance (Imemb) may be estimated from the voltage change (2ΔE) and the integrated change in current (ΔI). Additional signal processing techniques may be applied to improve the accuracy of the impedance estimate. For example, where the double-layer capacitance is estimated (as described above) or assumed to be a specified value, the determination of impedance may account for the double-layer capacitance.

Gated Amperometric Detection

In some examples, an analyte sensor circuit may be recurrently turned off and turned back on. During a period in which the sensor is turned off, an analyte (e.g., glucose) continues to interact with a sensor enzyme, which develops a signal that may be sensed. For, when a sensor circuit is off, glucose continues to react with glucose oxidase enzyme to produce hydrogen peroxide, which accumulates. When the sensor circuit is turned on, the accumulated hydrogen peroxide creates a much stronger signal than occurs without accumulation. Importantly, some interference materials, such as uric acid and acetaminophen, do not exhibit such an accumulation effect, so the signal-to-noise (or background or interference) ratio is improved. Thus, while the presence of acetaminophen (or other interference materials) may cause an error in a glucose sensor estimate (because the acetaminophen impacts the raw signal observed from the sensor), the impact of acetaminophen may be reduced by gating the analyte sensor circuit to increase the signal-to-noise ratio between the glucose signal and the interfering material. In an example, a test was performed using a sensor using gated and non-gated amperometry. A sensor in a solution with a glucose concentration of 156 mg/dL was exposed to acetaminophen to test the effect of gating the amperometry. With normal (non-gated) amperometry, a concentration of 1 mg/dL of acetaminophen resulted in an error of 3.19 mg/dL in the estimated glucose concentration. With normal gated amperometry, a concentration of 1 mg/dL of acetaminophen resulted in an error of 2.683 mg/dL in the estimated glucose concentration, which indicates that gating provides a system with greater acetaminophen tolerance (e.g., reduces the error due to the presence of acetaminophen at the sensor membrane).

Figure 8A:
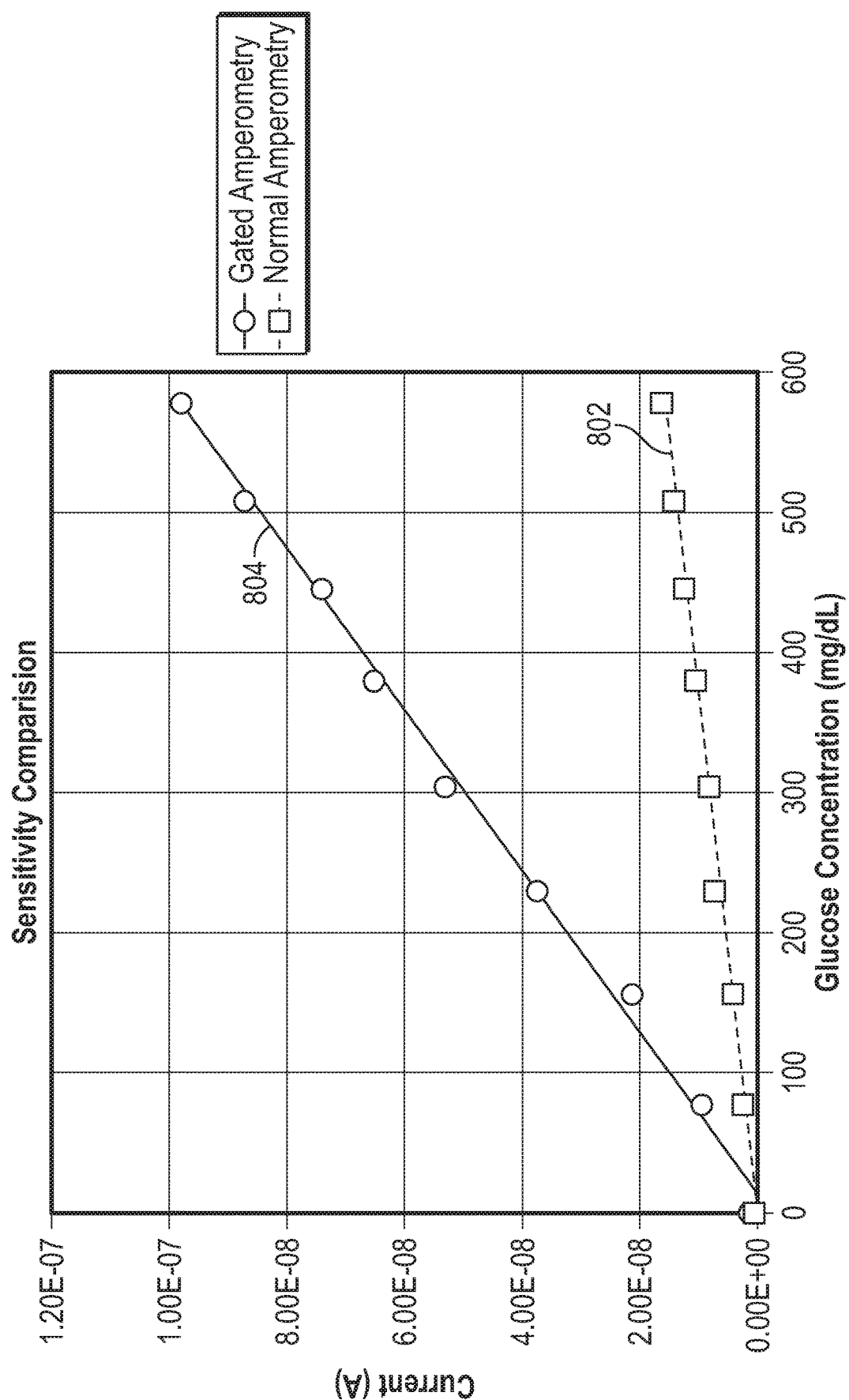
FIG. 8A is a graph that shows current plotted against glucose concentration for a sensor using a normal amperometry technique and a gated amperometry technique.

FIG. 8A shows current plotted against glucose concentration for a sensor. Data points were measured for a sensor using gated amperometry and normal (non-gated) amperometry across a range of glucose concentrations. The data shows the larger current response (which may be detected by an analyte sensor system) for gated amperometry than for normal amperometry. The data for normal amperometry shows a linear relationship between current and glucose concentration, indicated by line 802. The data for gated amperometry also shows a linear relationship between current and glucose concentration (indicated by line 804), but the slope is steeper, and the values are higher for gated amperometry. The steeper slope may allow for more effective differentiation between glucose concentration levels.

Figure 8B:
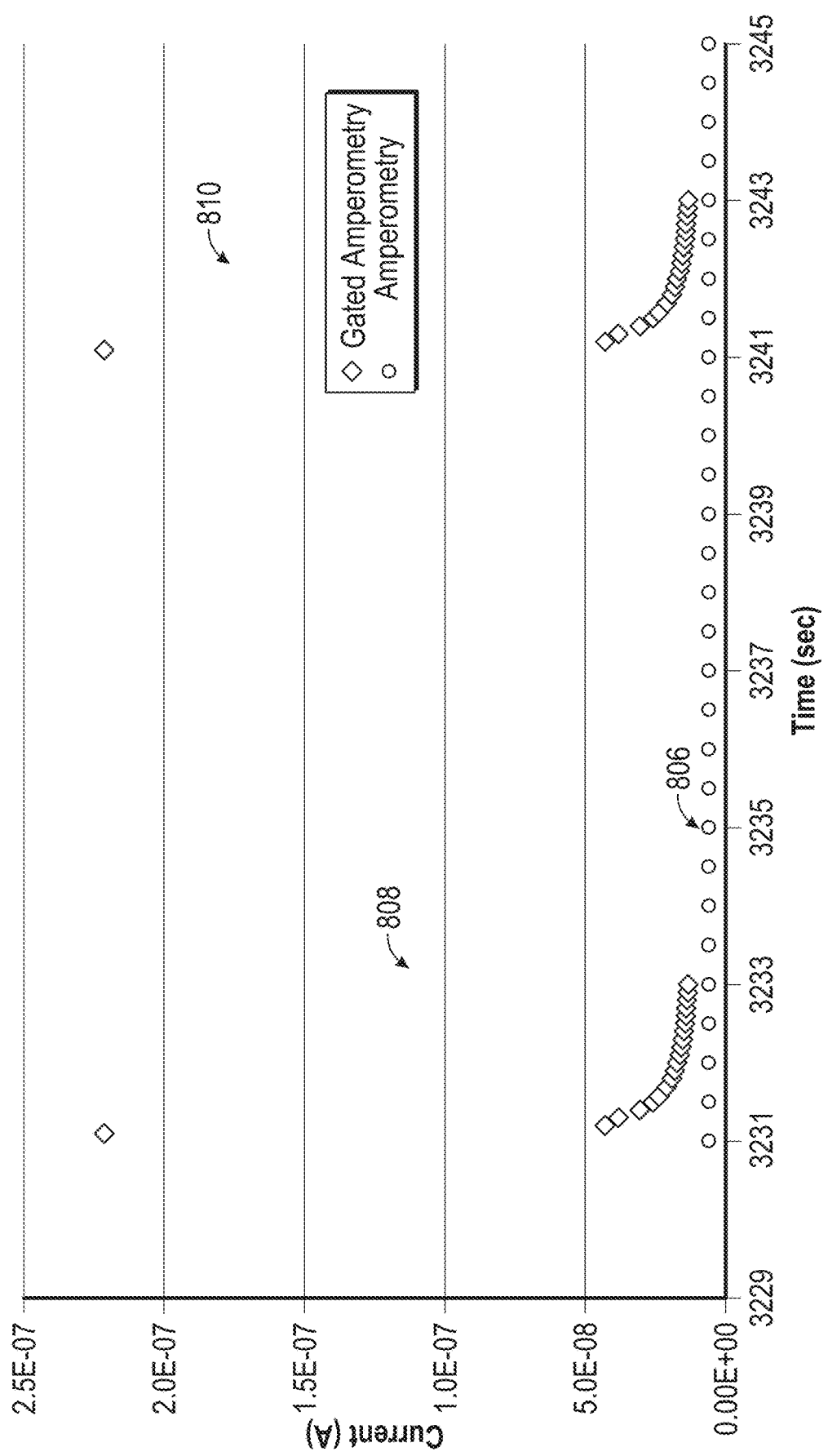
FIG. 8B is a graph that shows an example implementation of gated amperometry in an analyte sensor.

FIG. 8B is a graph that shows an example implementation of gated amperometry in an analyte sensor. The graph of FIG. 8B indicates time on the horizontal or x-axis and measured current from the analyte sensor on the vertical or y-axis. The data illustrated at FIG. 8B was captured with an analyte sensor in the presence of a constant concentration of analyte. A series 806 of samples indicate current responses of the analyte sensor measured using standard amperometry. In the illustrated example, the series 806 of samples are captured at rate of 2.5 samples per second. As shown, the series 806 of samples returns a constant current.

Series 808 and 810 show current responses of the analyte sensor according to gated amperometry. In this example, the bias voltage is applied to the analyte sensor for a two-second period and then removed for an eight-second period. For example, the series 808 of samples shows the current response of the sensor when the bias voltage is applied at 3231 seconds and then removed again at 3233 seconds. As shown, the initial sample of the series 808 returns a high current (~225 nA) that decays towards the current value of the standard amperometry series 806. Similarly, the series 810 of samples includes an initial sample at a high current (~224 nA) that also decays towards the current value of the standard amperometry series 806. The high initial current, for example, may be the result of the analyte sensor detecting hydrogen-peroxide generated from reactions at the sensor while the bias voltage was turned off. As the excess hydrogen-peroxide is reacted with the now-biased sensor, the sensor current decays towards the steady-state value indicated by the standard amperometry series 806.

Figure 8C:
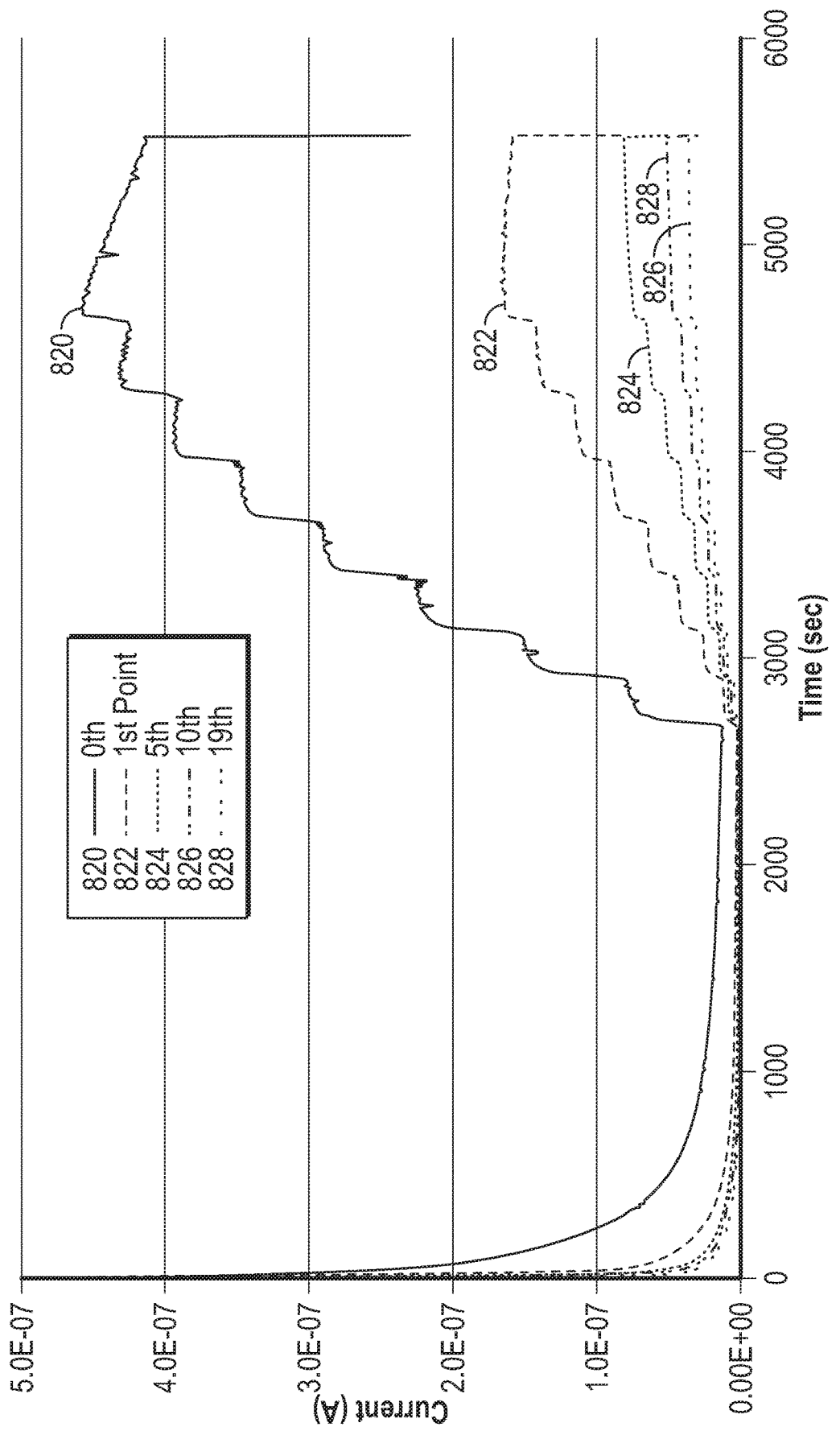
FIG. 8C is a graph showing example current responses of an analyte sensor operated using gated amperometry.

FIG. 8C is a graph showing example current responses of an analyte sensor operated using gated amperometry. The graph of FIG. 8C indicates time on the horizontal or x-axis and measured current from the analyte sensor on the vertical or y-axis. In the example of FIG. 8C, an analyte sensor was subjected to break-in in a buffer material having a constant analyte concentration. At about 2600 seconds, the analyte sensor was exposed to buffer materials with increasingly higher analyte concentrations. In this sample, the analyte sensor was exposed to each respective analyte concentration for about 200 seconds.

In the example of FIG. 8C, the analyte sensor was operated using gated amperometry in the manner indicated by FIG. 8B with the bias voltage applied for a two second period and then turned off for an eight second period. During the two second periods in which the bias voltage was applied, the current at the sensor was sampled at about 10 Hz (e.g., 1/100 ms). The curves 820, 822, 824, 826, 828 in FIG. 8C show the current response of the analyte sensor.

Curve 820 shows the response of the $0^{th}$ point indicating the first sample captured during each period in which the bias voltage is applied. Curve 822 shows the response of the $1^{st}$ point indicating the second sample captured during each period in which the bias voltage is applied. Curve 824 shows the response of the $5^{th}$ point indicating the sixth sample captured during each period in which the bias voltage is applied. Curve 826 shows the response of the $10^{th}$ point indicating the eleventh sample captured during each period in which the bias voltage is applied. Curve 828 shows the response of the $19^{th}$ point indicating the twentieth sample captured during each period in which the bias voltage is applied. As shown, the current level corresponding to early points is high and then decays with later-captured points. FIG. 8C also shows that various different points exhibit a dependence on the analyte concentration present at the sensor.

Figure 8D:
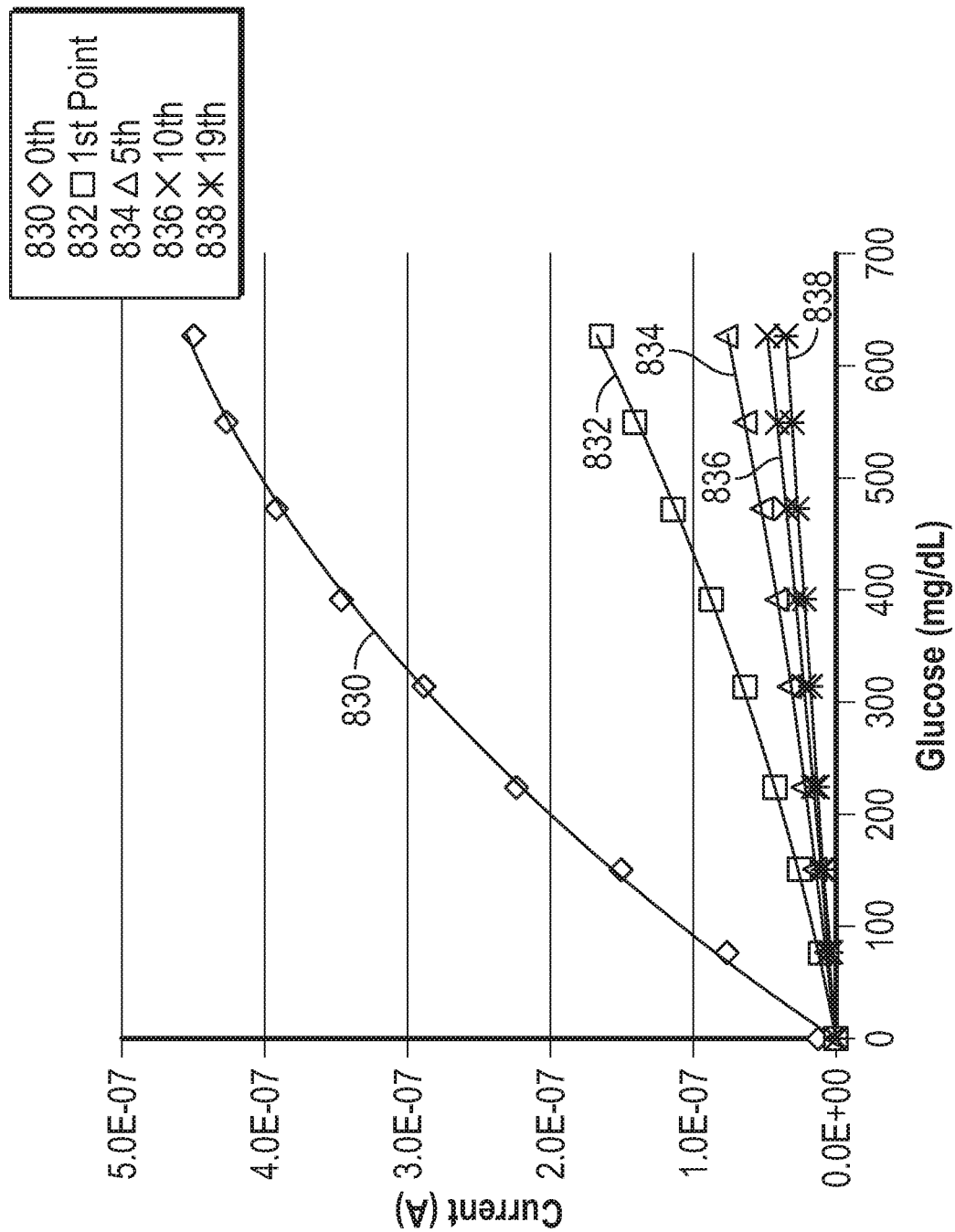
FIGS. 8D and 8E are graphs showing sensitivity of the example current responses illustrated in FIG. 8C.
Figure 8E:
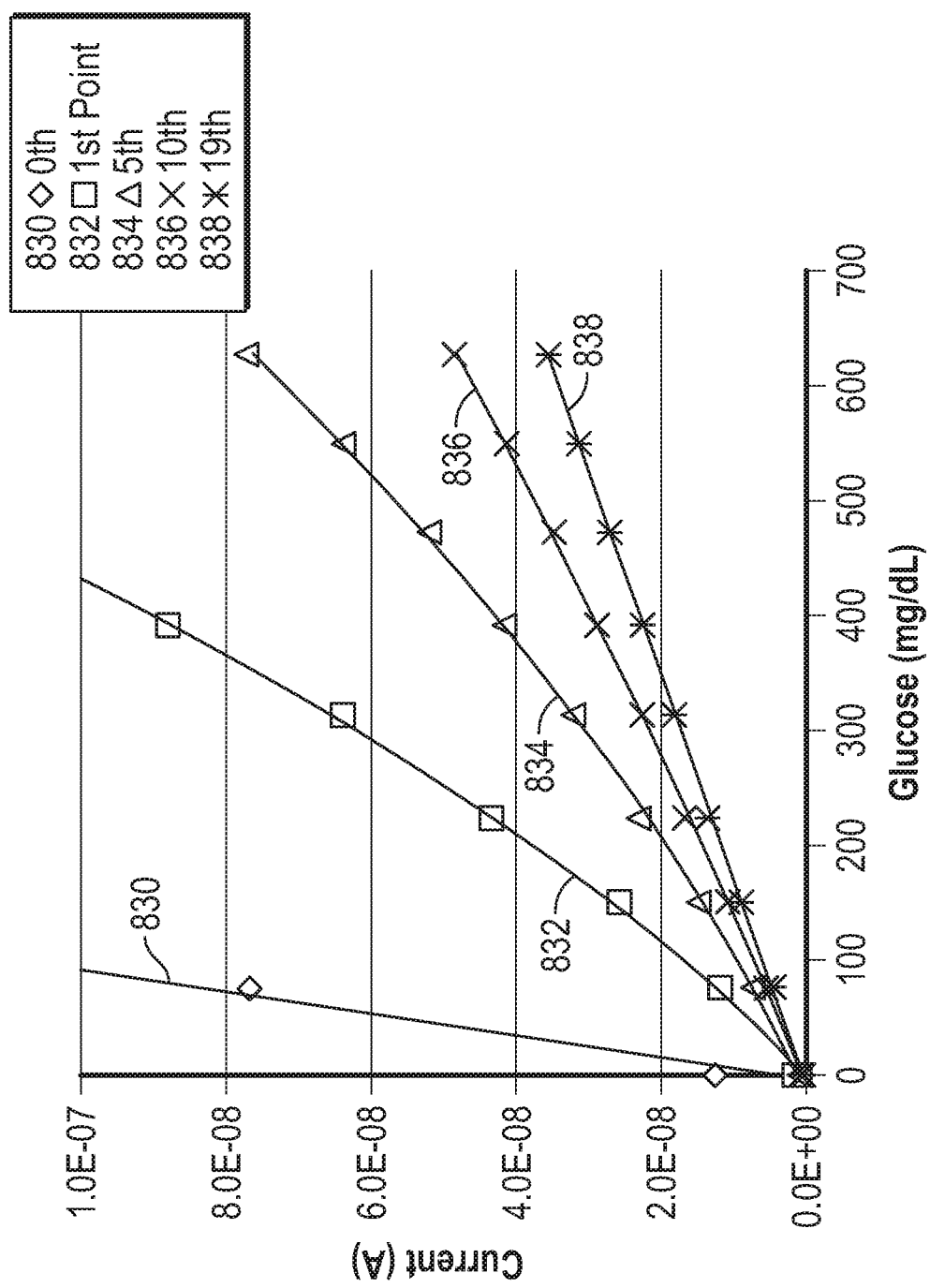

FIGS. 8D and 8E are graphs showing sensitivity of the example current responses illustrated in FIG. 8C. The graph of FIGS. 8D and 8E indicate analyte concentration (glucose in this example) on the horizontal or x-axis and measured current from the analyte sensor on the vertical or y-axis. A curve 830 shows the sensitivity of the $0^{th}$ point or first sample captured during each period in which the bias voltage is applied. A curve 832 shows the sensitivity of the $1^{st}$ point or second sample captured during each period in which the bias voltage is applied. A curve 834 shows the sensitivity of the $5^{th}$ point or sixth sample captured during each period in which the bias voltage is applied. A curve 836 shows the sensitivity of the $10^{th}$ point or eleventh sample captured during each period in which the bias voltage is applied. A curve 838 shows the sensitivity of the $19^{th}$ point or twentieth sample captured during each period in which the bias voltage is applied. FIGS. 8D and 8E show the curves 830, 832, 834, 836, 838 on different scales. For example, in FIG. 8D, the scale of the vertical axis indicating current is from zero to about 500 nA. In FIG. 8E, the scale of the vertical axis indicating current is from zero to about 100 nA.

Figure 8F:
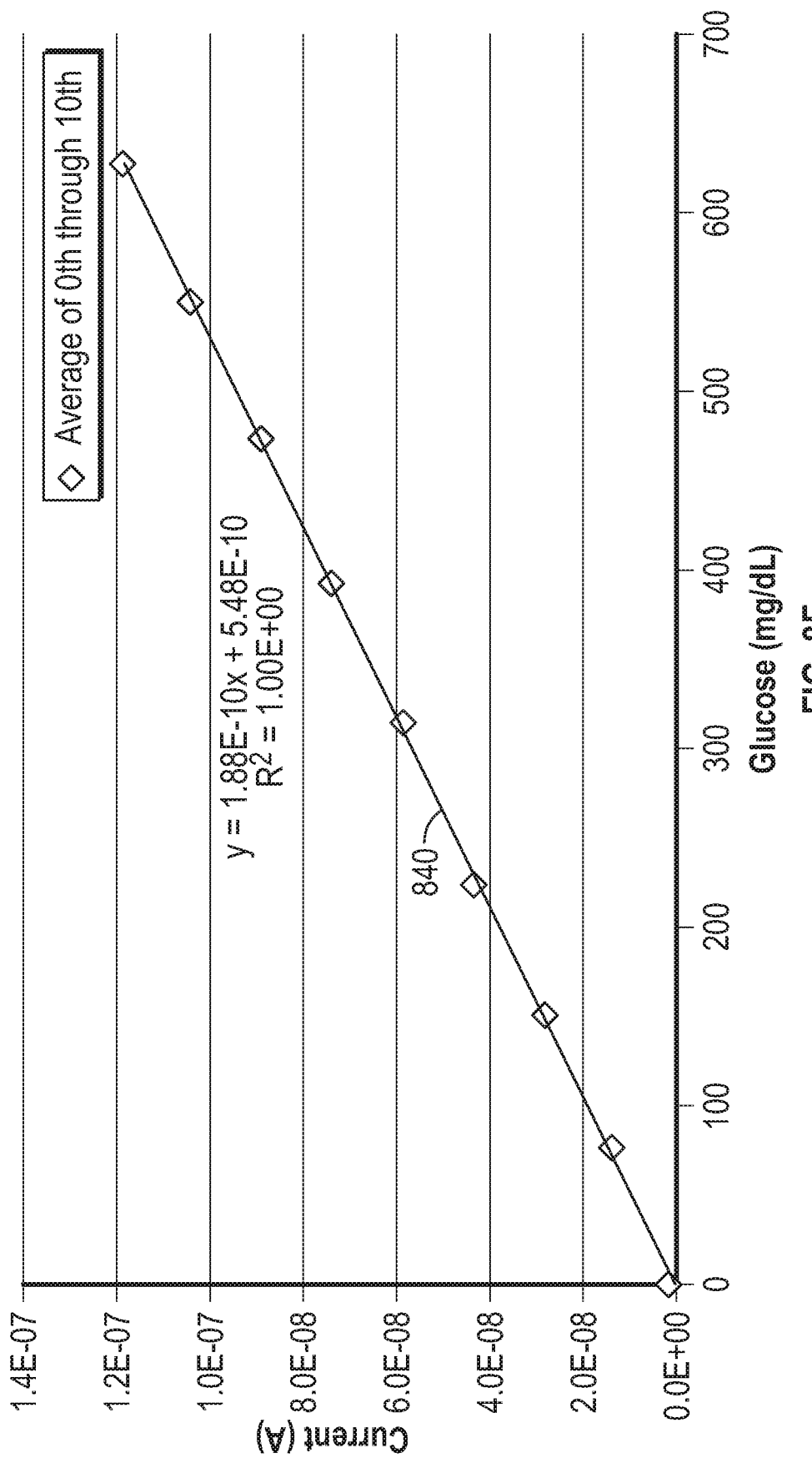
FIG. 8F is a graph showing sensitivity of the example current responses illustrated in FIG. 8C averaged over the $0^{th}$ through the $10^{th}$ point.

FIG. 8F is a graph showing sensitivity of the example current responses illustrated in FIG. 8C averaged over the $0^{th}$ through the $10^{th}$ point. The graph of FIG. 8F indicates analyte concentration (glucose in this example) on the horizontal or x-axis and measured current from the analyte sensor on the vertical or y-axis. A curve 840 shows the sensitivity of an average of the $0^{th}$ point through the $10^{th}$ point. In some examples, gated amperometry can be used to measure analyte concentration using an average of samples gathered while a bias voltage is applied in this way. Although the $0^{th}$ through the $10^{th}$ points are used herein, other combinations can also be used.

Figure 8G:
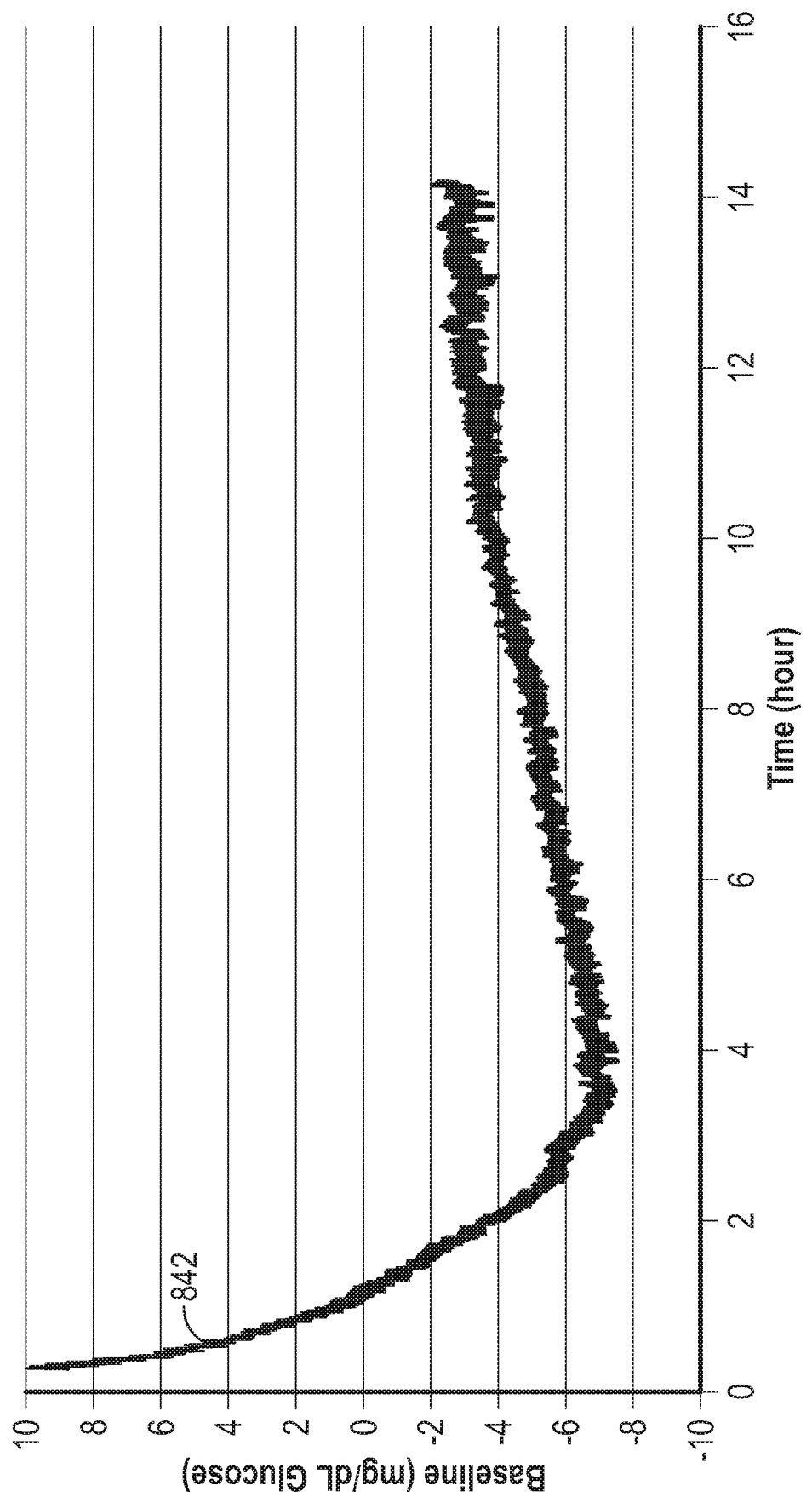
FIG. 8G is a graph showing a baseline curve derived from the example current responses of FIG. 8C averaged over the $0^{th}$ through the $10^{th}$ point.

FIG. 8G is a graph showing a baseline curve 842 derived from the example current responses of FIG. 8C averaged over the $0^{th}$ through the $10^{th}$ point. The graph of FIG. 8G indicates time on the horizontal or x-axis and baseline analyte concentration on the vertical or y-axis. The baseline analyte concentration is a concentration of analyte (glucose in this example) corresponding to a zero level of current at the analyte sensor. As shown by the curve 842, the gated amperometry methods described herein can result in a relatively constant baseline concentration after about 2 hours.

Figure 8H:
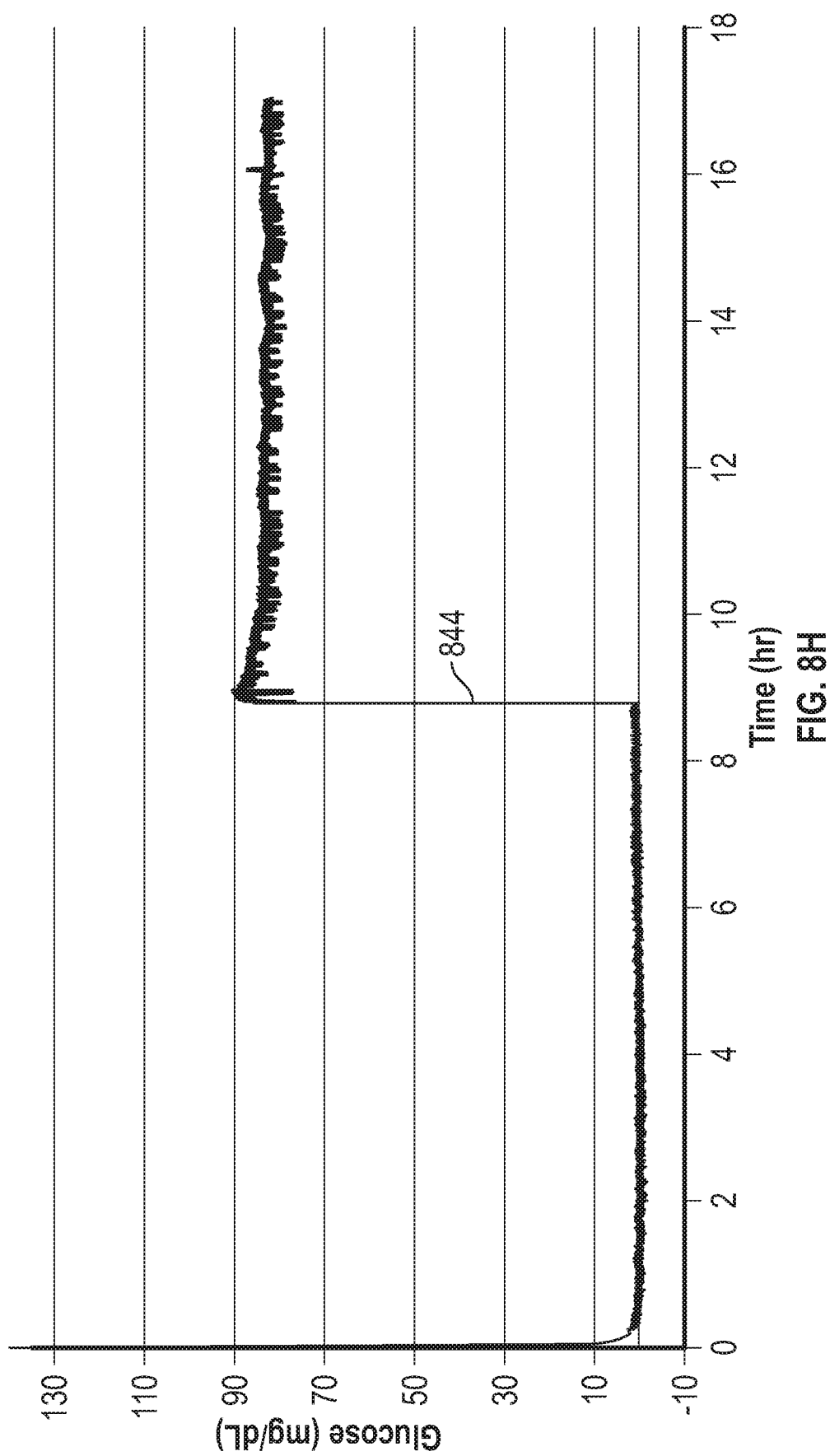
FIG. 8H is a graph showing a span curve of an analyte sensor operated using gated amperometry as described herein.

FIG. 8H is a graph showing a span curve 844 of an analyte sensor operated using gated amperometry as described herein. The graph of FIG. 8H indicates time on the horizontal or x-axis and analyte concentration on the vertical or y-axis (in this example, glucose concentration). The span curve 844 indicates the glucose concentration values received from the analyte sensor based on the average of the $0^{th}$ through the $10^{th}$ point as described herein. In this example, the analyte sensor was initially exposed to a buffer having a glucose concentration of zero. At about 9 hours, the analyte sensor was exposed to a buffer having an analyte concentration of about 85 ml/dL. As shown, the analyte concentration values provided by the analyte sensor remain roughly constant.

Figure 8I:
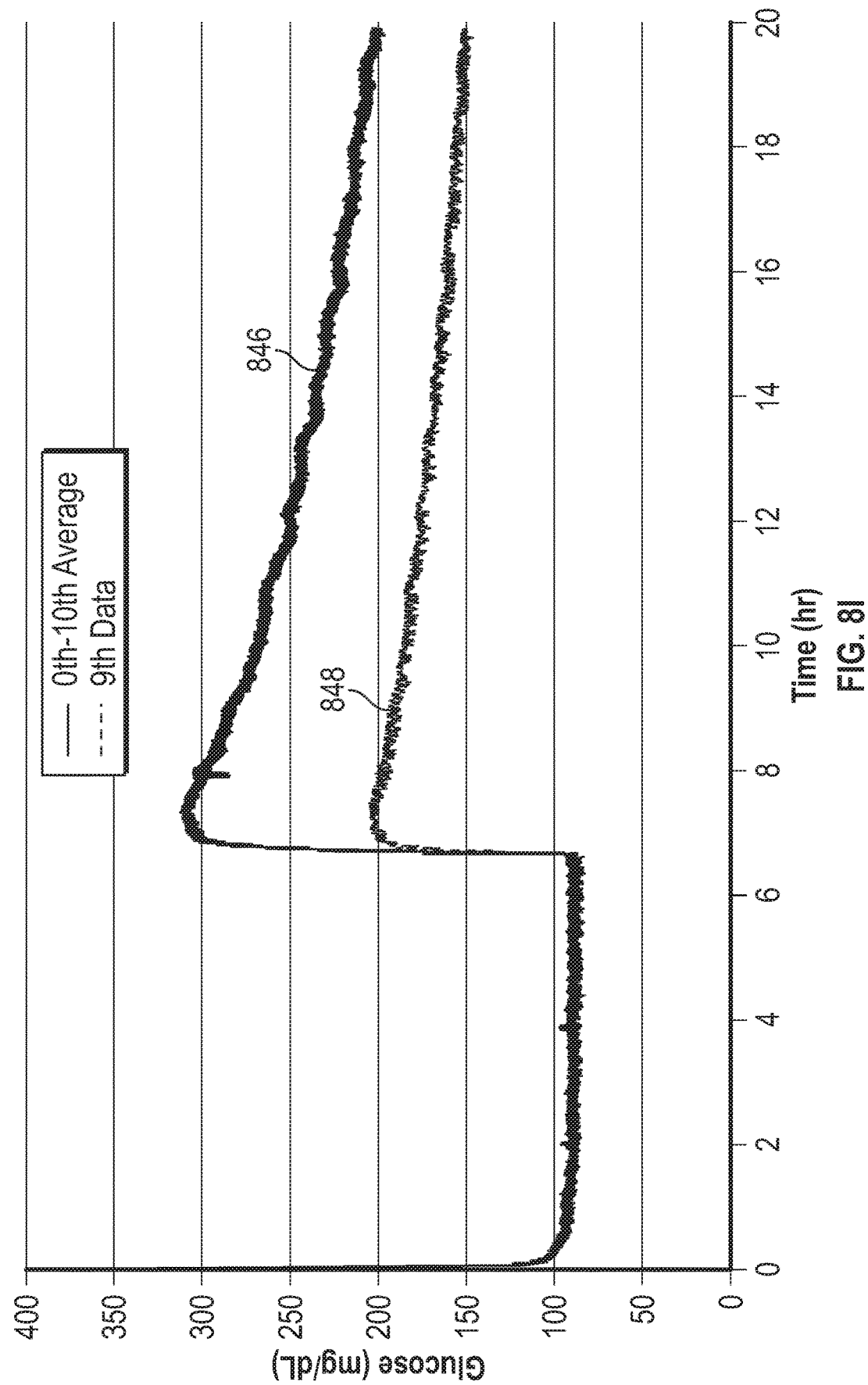
FIG. 8I is a graph showing span curves of an analyte sensor operated using gated amperometry in the presence of acetaminophen.

FIG. 8I is a graph showing span curves 846, 848 of an analyte sensor operated using gated amperometry in the presence of acetaminophen. The span curve 846 shows the response of the $19^{th}$ point sample, as described herein. The span curve 848 shows an average of the $0^{th}$ through the $10^{th}$ point samples, as described herein. Because the sensor current decays towards the steady state voltage, the 19th point is closer to the steady state glucose reading (e.g., using standard amperometry). In the example of FIG. 8I, the analyte sensor was exposed to a buffer with a glucose concentration of about 85 ml/dL until about 6.5 second after which the analyte sensor was exposed to a buffer with a glucose concentration of about 150 ml/dL. As shown, the span curve 848 for the average of the $0^{th}$ through $10^{th}$ points is flatter than the span curve 846 for the $19^{th}$ point.

Humidity Detection

An estimated impedance of a moisture-sensitive portion of an analyte sensor may be used to detect humidity. For example, an estimated membrane impedance (e.g., an estimated membrane impedance determined as described above) may provide an indication of exposure of an analyte sensor to a relatively humid environment (compared to a baseline relative humidity). Environments with varying humidity may occur, for example, in manufacturing, storage, transportation (e.g., between manufacturing steps, or en route to a distributor or end user), or with an end user (e.g., if a sensor package is opened but the sensor is not used for a substantial period of time after opening).

An analyte sensor (such as the sensor shown in FIGS. 3A-3C, described above) typically includes an anode (e.g., working electrode), a cathode (e.g., reference electrode), and at least one membrane covering the anode, cathode, or both. The membrane typically includes hydrophilic domains, in which ions may reside and move, which makes the membrane electrically conductive. The membrane conductivity (or resistivity or impedance) may be indicative of the humidity of the environment to which the membrane has been exposed (e.g., because the membrane absorbs water vapor, which makes it more conductive). An impedance measurement may be made by applying a small amplitude (e.g., 1-200 millivolts) excitation pulse or AC signal to a sensor circuit. An impedance estimate may be determined from an observed current response in the sensor circuit, in combination with one or more known voltage characteristics of the injected signal or pulse (e.g., an impedance estimate may be determined based on Ohms law).

In some examples, a plurality of impedance estimates (or measurements from which an impedance estimate may be determined) may be tracked over time, which may provide an indication of the humidity of the environment to which the sensor has been exposed, or the relative humidity of the sensor environment, or both.

The exposure of an analyte sensor to humidity may impact the performance of the sensor. In some examples, a sensor system parameter (e.g., a glucose sensitivity, or glucose sensitivity profile over time) may be adjusted based upon an estimated humidity exposure (e.g., the sensor system output may be compensated for pre-implantation humidity exposure). In some examples, a system may generate an alert or warning indicating that a sensor has been exposed to excessive humidity, or to excessively dry conditions. For example, a system may inform a user that a sensor should not be used.

Figure 9:
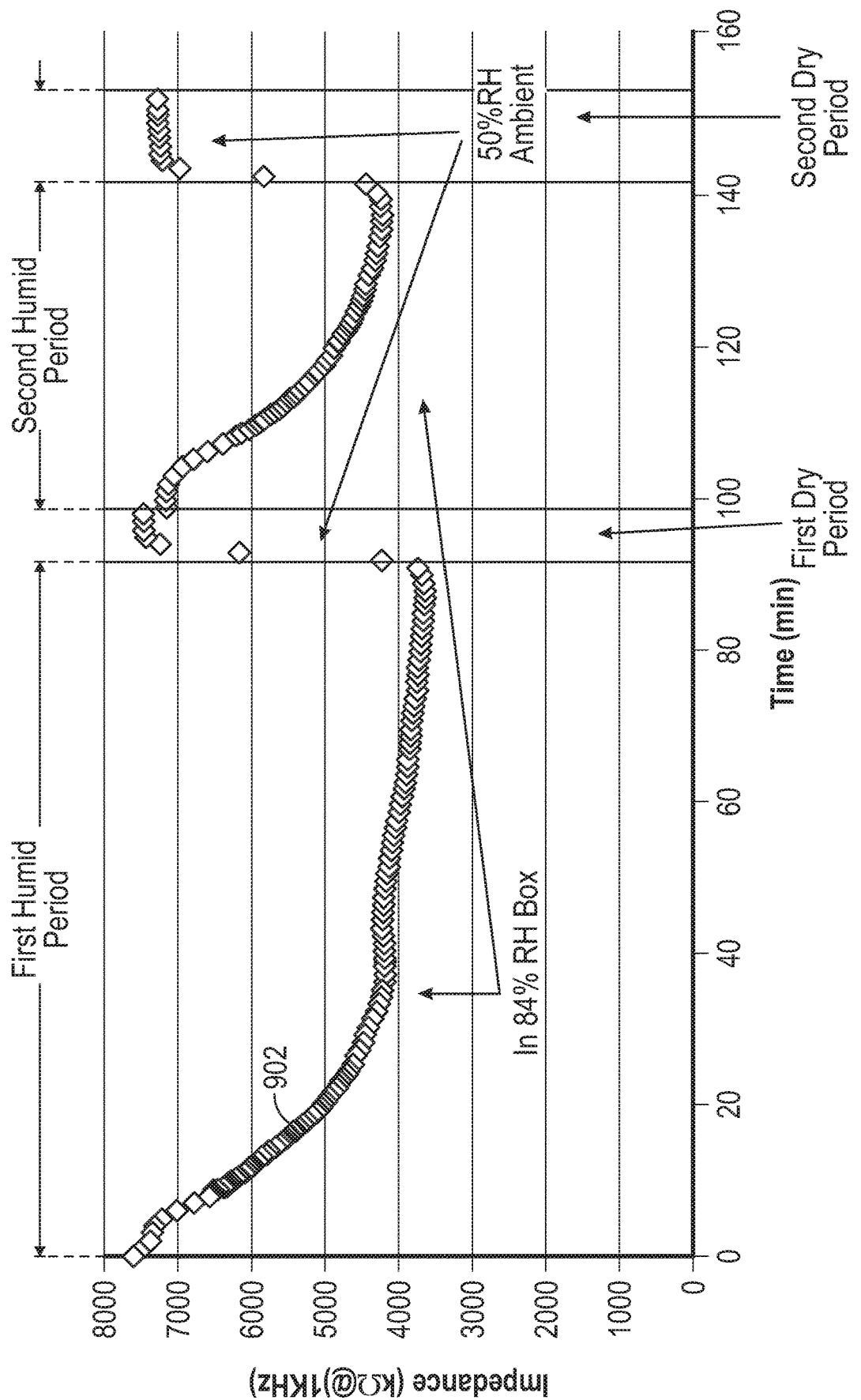
FIG. 9 is a graph that shows measured impedance values plotted against time.

FIG. 9 is a graph that shows measured impedance values 902 plotted against time. The impedance values 902 are plotted against minutes, but in other examples may be plotted against days or weeks. The data is from a benchtop experiment, with controlled-humidity environments at 84% relative humidity and 50% relative humidity but is representative of the response of a sensor in actual environments.

At the beginning of a first humid period (which extends from 0 to 93 minutes), the analyte sensor has an estimated impedance (e.g., derived using voltage and current measurements, and Ohm's law) of about 7700 kiloohms (kΩ), at 1 kilohertz. As the sensor absorbs moisture, the impedance during the first period trends downward until it reaches about 3800 kiloohms at 93 minutes. At 93 minutes, the analyte sensor was exposed to a 50% relative humidity ambient environment during a first dry period (from 93 minutes to 98 minutes). As the sensor dried out (e.g., as water evaporated from the sensor membrane and entered the relatively dry ambient environment), the impedance of the sensor quickly trends back up to about 7500 kiloohms. After the first dry period, the sensor was reintroduced to an 84% relative humidity environment for a second humid period (from 98 minutes until 140 minutes), and the sensor impedance fell back down to about 4200 kiloohms. At 140 minutes, the sensor was again exposed to a 50% relative humidity ambient environment, and the estimated impedance rose to over 7000 kiloohms. The data in FIG. 9 illustrates that impedance may be used to track exposure to humidity. Humidity information, such as the humidity information shown in FIG. 9, may be used to determine an alert or warning (e.g., "Sensor damaged") or to adjust the performance of the sensor (e.g., compensate for impedance changes caused by humidity). In some examples, an impedance prior to implantation may be used to compensate an analyte sensitivity (e.g., glucose sensitivity).

While the sensor is generally referred to in this disclosure as an analyte sensor, in other examples, the sensor (e.g., the sensor 34 in FIGS. 3A-3B) may be used as a humidity sensor.

In some examples, a sensor may be integrated into "smart" packaging (of an analyte sensor, or of another device), and humidity in the package, or outside or around the package, may be sensed or tracked.

In some examples, an analyte sensor system or smart packaging may include a memory circuit, which may store impedance information. The impedance information may be stored with time information, which may provide a history of the humidity exposure of the device or packaging. In various examples, impedance may be detected and stored several times a minute, once a minute, several times an hour, once an hour, several times a day (e.g., every six hours), once a day, on a multi-day interval (e.g., every two days, three days, five days, or ten days), once a week, several times a month (e.g. semi-monthly), or once a month. The humidity history information may be used to determine an alert or alarm (e.g., declare that a product is damaged or potentially damaged), or may be presented on a user interface for evaluation by a user, or may be sent over a network (such as the network shown in FIG. 1) for remote processing or evaluation.

Estimated Sensor Sensitivity Methods and MARD Improvements

In various examples, impedance may be used alone, or in combination with one or more other factors, to determine a sensor sensitivity ($m_t$). While impedance may be used as a surrogate for sensitivity, e.g., to account for drift, many factors may influence impedance. For example, fluctuations in temperature may introduce impedance fluctuations in an in vivo ionic environment. A sensitivity determination may be improved by combining additional information with impedance.

Any of the techniques described herein for determining an impedance parameter may be used to obtain an estimated impedance parameter. For example, an impedance parameter may be determined using an impulse-response method to measure membrane impedance. In an example, impedance may be determined based on an integrated pulse-current (PI) as driven by a square wave pulse supplied by sensor electronics. The relationship between integrated pulse-current (PI) and membrane impedance ($R_{RL}$) is deterministic.

Using impedance alone, sensitivity may be determined based on the integrated pulse current using the following equation (denoted "IMPD"):

$$\hat{m}_t = PI \cdot (a_1 + a_2 \cdot \log(t))$$

In the equation above, and the other examples below, the values denoted $a_x$ (e.g., $a_1$, $a_2$, $a_3$, etc.) may be experimentally determined using a number of similar sensors.

Using impedance in combination with a calibration curve (CC) for the sensor (which may for example be an experimentally-determined relationship (e.g., slope) between analyte level and measured current), sensitivity may be determined based on the following equation (denoted "IMPD+CC"):

$$\hat{m}_t = PI \cdot (a_1 + a_2 \cdot \log(t)) \cdot \left(1 + \frac{a_3 \cdot CC + a_4}{100}\right)$$

In products made by Dexcom, the calibration curve (CC) may be a Calcheck slope determined for a particular sensor, or for a population of sensors.

Using impedance in combination with transmitter temperature, sensitivity ($m_t$) may be determined from the equation (denoted "IMPD+T"):

$$\hat{m}_t = PI \cdot (a_1 + a_2 \cdot \log(t) + a_3 \cdot T)$$

or from the equation:

$$\hat{m}_t = PI \cdot (a_1 + a_2 \cdot \log(t)) \cdot (a_3 + a_4 \cdot T)$$

Using impedance in combination with transmitter temperature (T) and a calibration slope (CC), sensitivity ($m_t$) may be determined from the equation (denoted "IMPD+T+CC"):

$$\hat{m}_t = PI \cdot (a_1 + a_2 \cdot \log(t) + a_3 \cdot T) \cdot \left(1 + \frac{a_4 \cdot CC + a_5}{100}\right)$$

or from the equation:

$$\hat{m}_t = PI \cdot (a_1 + a_2 \cdot \log(t)) + (a_3 + a_4 \cdot T) \cdot \left(1 + \frac{a_5 \cdot CC + a_6}{100}\right)$$

In another example, an empirical linear relationship may also be pursued without making any assumption about the underlying relationship between different physical variables, and sensitivity ($m_t$) may be determined from the equation:

$$\hat{m}_t = a_1 + a_2 \cdot CC + a_3 \cdot \log(t) + a_4 \cdot PI + a_5 \cdot T$$

In all the equations above, the integrated pulse-current PI may be replaced directly by RL membrane resistance (in unit of kΩ):

$$R_{RL}^{-1} \approx \frac{PI}{8541.6 - 147.6 \cdot PI}$$

Note that the inverse of membrane resistance (1/R) is conductance. Sensitivity ($m_t$) may be determined from the conductance equation (denoted "Cdut+T+CC"):

$$\hat{m}_t = R_{RL}^{-1} \cdot (a_1 + a_2 \cdot \log(t)) + (a_3 + a_4 \cdot T) \cdot \left(1 + \frac{a_5 \cdot CC + a_6}{100}\right)$$

In some examples, the conversion parameters in $R_{RL}^{-1}$ may be optimized empirically, and sensitivity ($m_t$) may be determined from the equation:

$$\hat{m}_t = a_1 + [a_2 \cdot CC + a_3] \cdot [1 - \exp(-a_4 \cdot t)] + \frac{PI}{a_5 \cdot PI + a_6} + a_7 \cdot T$$

In some examples, a temperature may be determined using impedance. Methods for determining a temperature (e.g., the temperature of a sensor working electrode) using are described, for example, in U.S. Patent Publication No. 2012/0262298 and U.S. Patent Application No. 62/620,775, both of which are incorporated by reference in their entirety. In some examples, a subcutaneous temperature (e.g., an estimate of an analyte sensor working electrode temperature) may be determined from a non-subcutaneous temperature sensor signal (e.g., transmitter temperature) using a partial differential equation (PDE) model. A PDE approach to temperature compensation may make the system more accurate, for example by accounting for the fact that the rate of change of temperature in external electronics (e.g., a CGM transmitter) is higher than the rate of change of temperature of subcutaneous tissue or fluids. In some examples, Green's function (GF) of the full PDE model may be used to filter a non-subcutaneous temperature (e.g., transmitter temperature (TTx)) linearly and causally, with the sensor working electrode temperature as the output. Because the PDE model assumes fixed parameters, it can be deemed a linear time-invariant (LTI) system, whose GF is also the impulse response function (IRF) of that LTI system. Two forms of GF can be obtained, one of which is by empirically solving a least-square fit for the IRF, and the second by a parametric fit to the empirical IRF which requires only three parameters. Both IRF solutions resulted in less than 0.1° C. difference from the sensor working electrode temperature predicted by solving the full PDE. Using Green's function may improve the performance of the sensor system (e.g., reduce power consumption or enable additional processing) because it avoids or reduces the need for a PDE solver (e.g., processor and software or firmware) in the sensor electronics. A PDE solver may consume significant power, increase cost of sensor electronics, or both.

Results of Experiments

Experiments were run to demonstrate the effectiveness of these approaches and the potential for improving the performance of an analyte sensor system. Based on forty-one (41) preliminary datasets, a Monte Carlo cross-validation procedure was performed on a commercially-available system (as a baseline) and four different techniques (described below) for improving the performance of an analyte sensor system. The results of the experiments are shown in FIGS. 10A-10F and show that the prediction errors of in vivo glucose sensitivity can be significantly improved using the combination of different physical measurements, such as impedance, temperature, and a calibration curve.

For a baseline comparison, a standard commercial factory-calibrated Dexcom G6 sensor system was used, without in vivo calibration.

A first technique based sensitivity drift compensation on impedance measurement alone using the relationship (IMPD) described above.

A second technique based sensitivity drift compensation on both impedance and calibration curve using the relationship (IMPD+CC) described above.

A third technique based sensitivity drift compensation on both impedance and temperature using the relationship (IMPD+T) described above.

A fourth technique based sensitivity drift compensation on impedance, temperature and a calibration curve, using the relationship (IMPD+CC+T) described above.

For the purpose of comparison, curves were also generated for a factory calibration approach with wedge parameters optimized locally using the same informal datasets as those used in training the other prototype algorithms ("FC Local").

FIGS. 10A to 10F show the cumulative distribution functions (CDF), for various metrics, from 1000 rounds of randomizations.

Figure 10A:
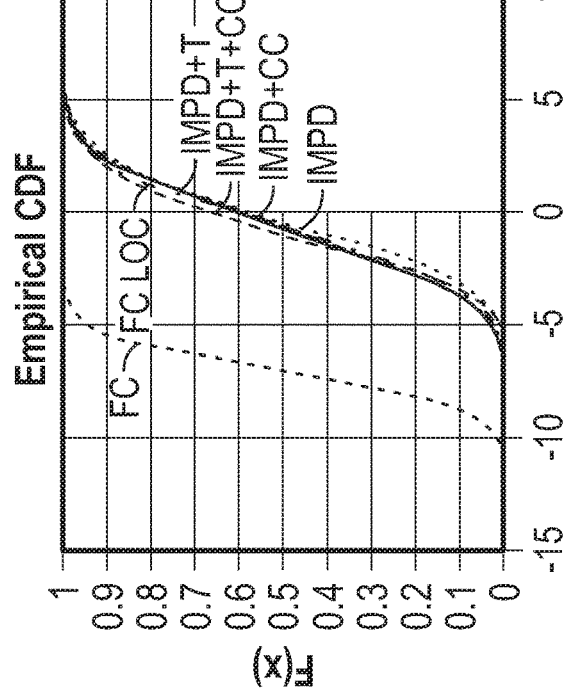
FIG. 10A shows empirical cumulative distribution function of the mean absolute relative difference (MRD) for a variety of compensation techniques.

FIG. 10A shows empirical cumulative distribution function of the mean absolute relative difference (MARD). The MARD is a measure of error. Thus, with respect to sensor system performance, a lower MARD is more desirable than a higher MARD, because the sensor data will be more accurate (e.g., include less error compared to a gold standard). The F(x) on the Y axis is the proportion of randomizations that produced a particular MARD.

Each of the drift compensation techniques provided a lower MARD than the baseline factory-calibrated (FC) sensor. The technique that used impedance, a calibration curve (CalCheck), and temperature produced the smallest MARD.

Figure 10B:
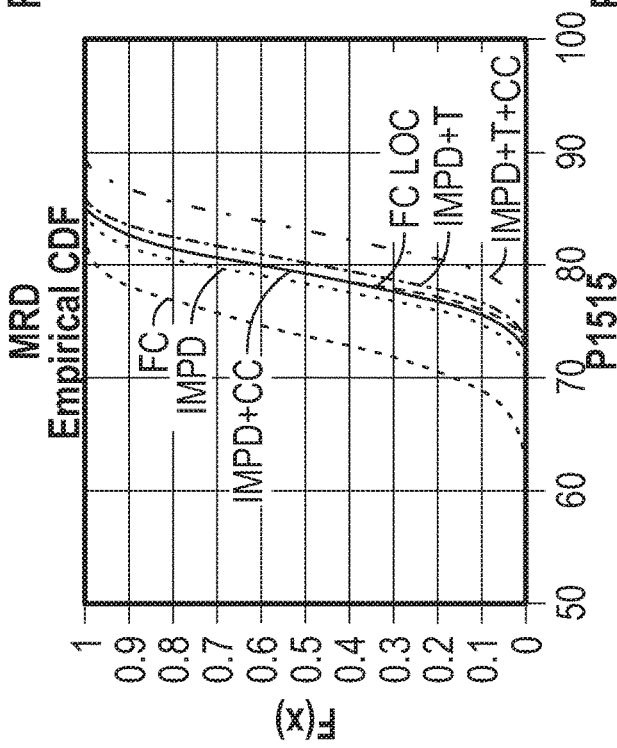
FIG. 10B shows the empirical cumulative distribution function of the mean relative difference (MRD).

FIG. 10B shows the empirical cumulative distribution function or the mean relative difference (MRD). An MRD value closer to zero is more desirable. The various improvement techniques produced highly clustered MRD values, and each technique represents an improvement over the factory-calibrated (FC) result.

Figure 10C:
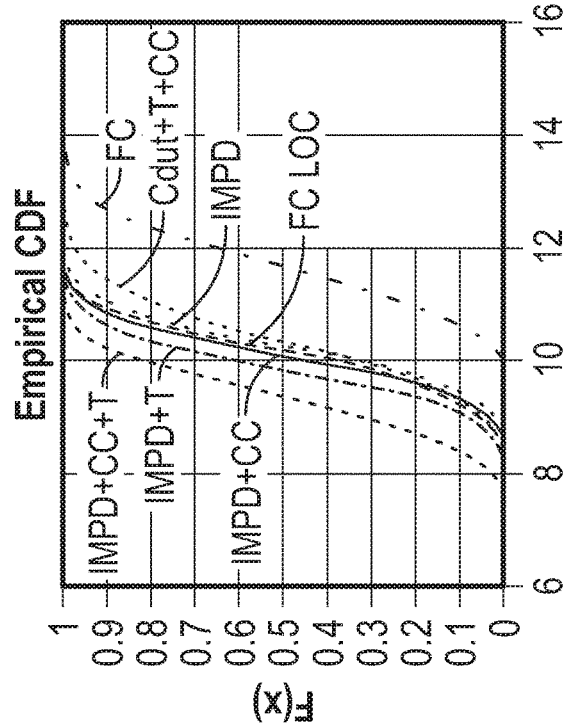
FIG. 10C shows the empirical cumulative distribution function of the relative distance (RD).

FIG. 10C shows the empirical cumulative distribution function or the relative distance (RD). An RD value closer to zero is more desirable. The various improvement techniques produced highly clustered MRD values, and each technique represents an improvement over the factory-calibrated (FC) result.

Figure 10D:
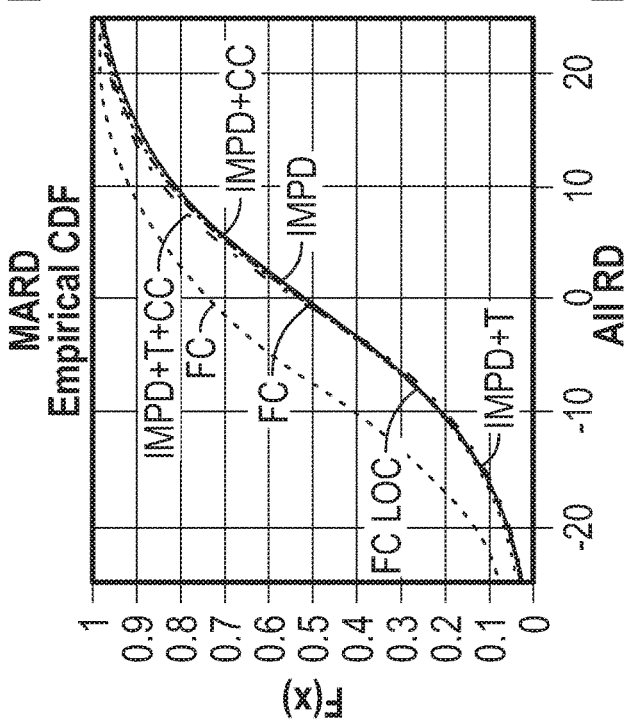
FIGS. 10D, 10E, and 10F show the empirical cumulative distribution function for p1515, p2020, and p4040.
Figure 10E:
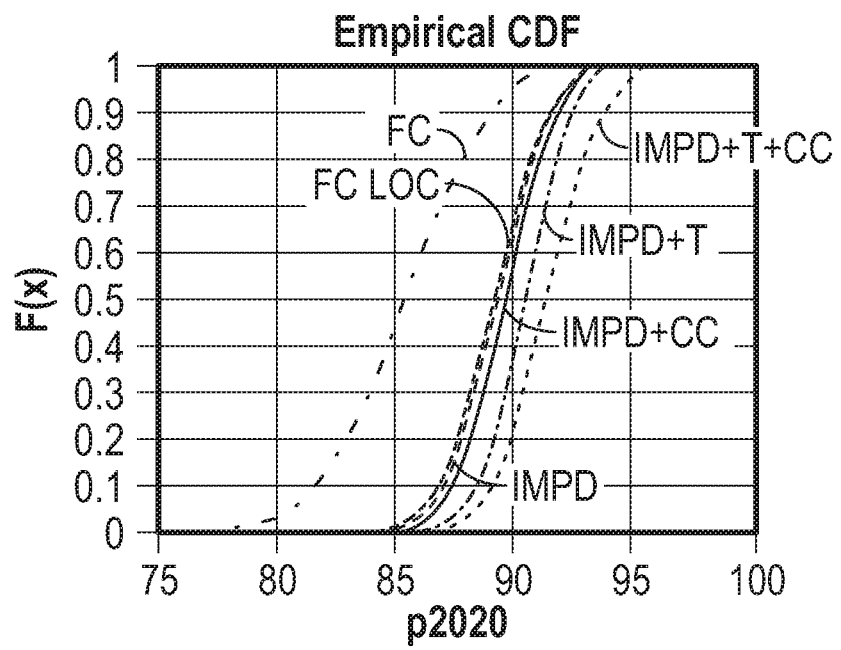
Figure 10F:
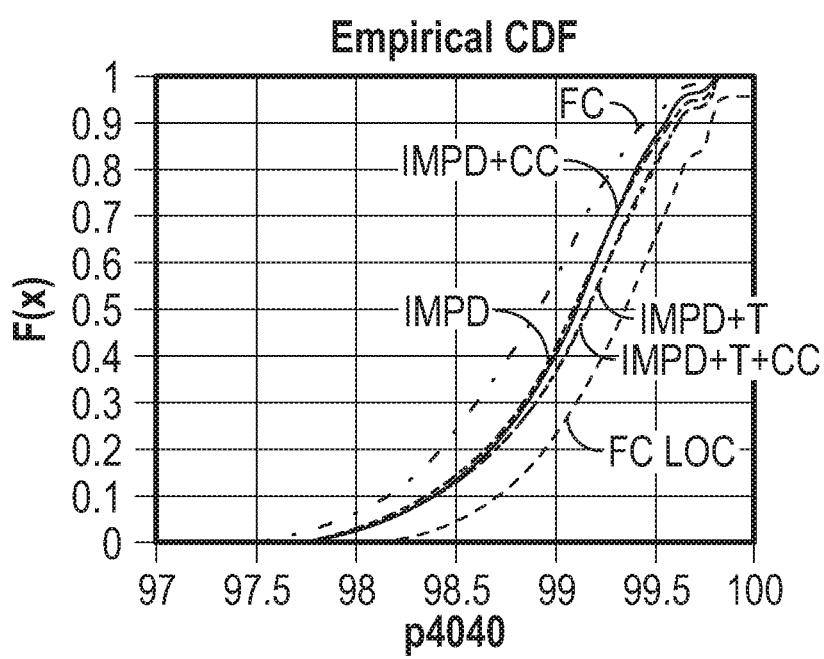

FIGS. 10D, 10E, and 10F show the empirical cumulative distribution function for p1515, p2020, and p4040. The charts indicate the percentage of randomizations that will fall within respective fifteen percent (±15% for FIG. 10D), twenty percent (±20% for FIG. 10E), or forty percent (±15% for FIG. 10F), of an actual blood glucose value. A higher value is better, as it indicates that a larger percentage of sensors will fall within a specified error range. Each of the four techniques improved the performance of the analyte sensor system. FIG. 10G provides data that shows the performance improvement achieved by various compensation techniques described above.

Using a compensation technique to account for factors such as temperature, in vivo environment changes, and damage may improve sensor performance (e.g., lower the MARD for a sensor or a sensor population), or may improve manufacturing yields (e.g., a smaller percentage of sensors may fail a performance test), or both.

Figure 11:
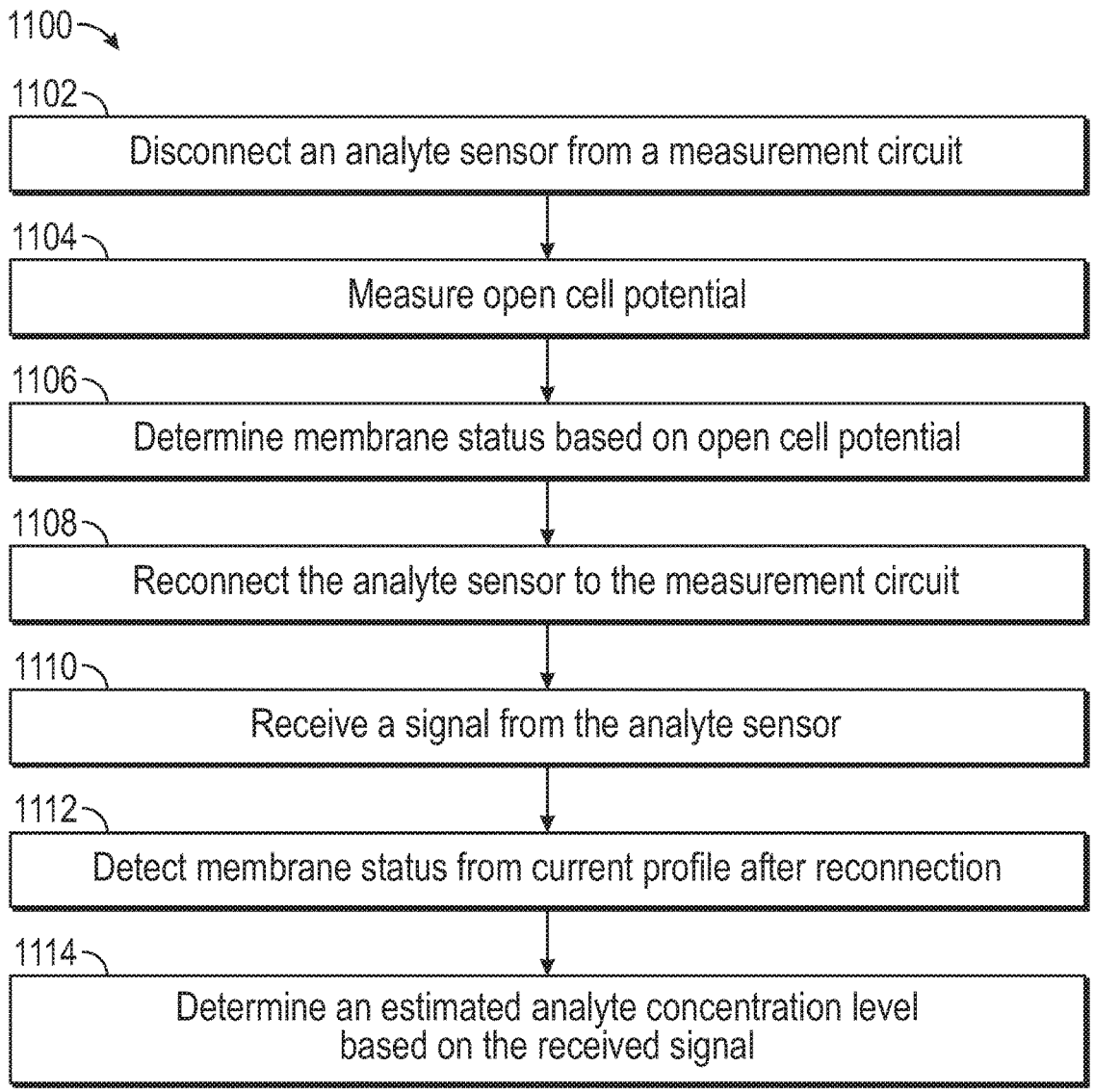
FIG. 11 is a flowchart illustration of a method that may include disconnecting an analyte sensor from a measurement circuit.
Figure 12:
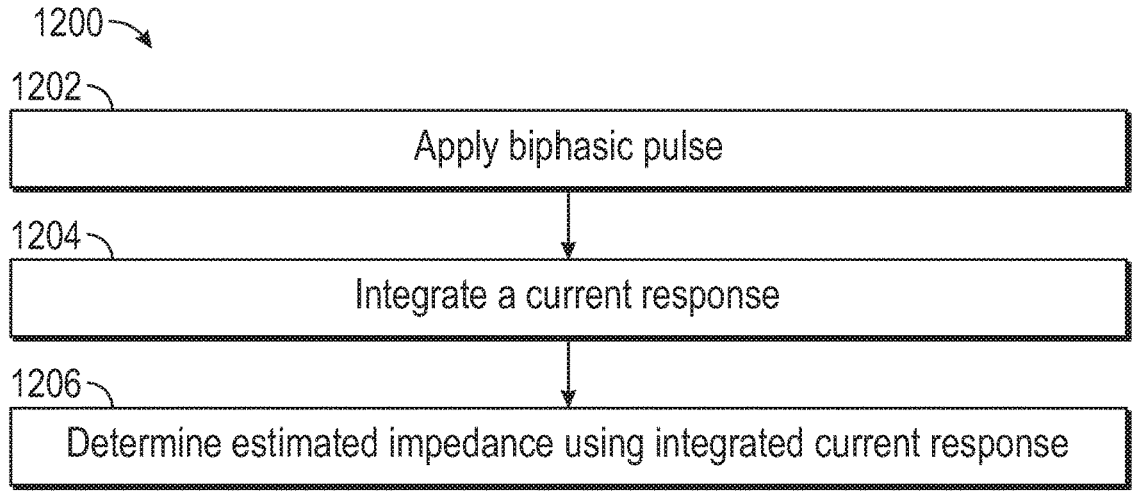
FIG. 12 is a flowchart illustration of a method that may include applying a biphasic pulse to a continuous analyte sensor circuit.

FIGS. 11 to 12 are flowchart illustrations that may be performed by sensor electronics (e.g., sensor electronics 106 in FIGS. 1 and 2) coupled to a sensor (e.g., sensor 104 in FIG. 1 or sensor 34 in FIGS. 3A-3B).

FIG. 11 is a flowchart illustration of a method 1100 that may include, at operation 1102, disconnecting an analyte sensor from a measurement circuit.

The method 1100 may include, at operation 1104, measuring one or more open cell potentials during the accumulation period. The method 1100 may include, at operation 1106, determining a membrane status based on one or more open cell potentials. In various examples, the membrane status may include an interference status (e.g., interference from acetaminophen), or a damage or abnormality status. For example, an abnormality or damage in a sensor membrane may be detected based upon an impedance characteristic (e.g., estimated sensor impedance, estimated membrane impedance, a first derivative of impedance, a second derivative impedance, or a fitted curve) determined from the one or more open cell potentials, or from a shape of an open cell vs. time curve.

The method 1100 may include, at operation 1108, reconnecting the analyte sensor to the measurement circuit after an accumulation period. The method 1100 may include using a gate circuit to disconnect and reconnect the analyte sensor.

The method 1100 may include, at operation 1110, receiving a signal from the analyte sensor, wherein the signal is indicative of an amount of charge accumulated on the analyte sensor during the accumulation period. Disconnecting and reconnecting (e.g., gating) an analyte sensor may improve the performance of a sensor system, for example because charge from an analyte reaction may increase during an accumulation period, resulting in a larger detectable current signal, whereas sources of interference or noise (e.g., acetaminophen) may not grow during the accumulation period. In some examples, the disconnection and reconnection of the analyte sensor improves a signal to interference ratio of the analyte sensor, as described above in the section titled "Gated Amperometric Detection."

The method 1100 may include, at operation 1112, determining a membrane status based on the analyte signal received after reconnection of the analyte sensor to the measurement circuit. In some examples, the method 1100 may include monitoring a current profile after reconnecting the analyte sensor and detecting a membrane status (e.g., membrane fault) using the current profile. In some examples, the method 1100 may include determining an impedance characteristic and detecting a membrane fault responsive to the impedance characteristic satisfying a fault condition (e.g., impedance characteristic below a threshold or resembling a damage template curve). In various examples, the impedance characteristic may be an estimated membrane impedance, a first derivative of impedance, a second derivative impedance, or a fitted curve.

The method 1100 may include, at operation 1114, determining an estimated analyte concentration level based on the received signal.

The method 1100 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to improve the signal to noise ration of a sensor system, or avoid reliance on inaccurate sensor readings from a sensor that has a damaged or abnormal membrane, or to determine an estimated analyte concentration level more accurately than conventional methods, based on one or more of the factors mentioned above.

FIG. 12 is a flowchart illustration of a method 1200 that may include, at operation 1202, applying a biphasic pulse to a continuous analyte sensor circuit. The method 1200 may include, at operation 1204, integrating a current response to the biphasic pulse, e.g., as described in reference to FIG. 7. The method 1200 may include, at operation 1206, determining an estimated impedance using the integrated current response, for example as shown in FIG. 7 and described in reference thereto. As described in various examples above, the estimated impedance may be used to detect a sensor membrane status or compensate for drift.

The method 1200 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to determine an impedance, detect a sensor membrane status (e.g., membrane fault), or determine an estimated analyte concentration level more accurately than conventional methods.

In some examples, the method 1100 or method 1200 may include compensating a sensor sensitivity using the determined impedance. In some examples, the method may include determining impedance using a signal at a frequency that avoid an effect of a double-layer membrane capacitance on the impedance. In some examples, the compensation may be based on impedance and one or more additional factors, such as temperature, a calibration curve (e.g., factory-determined calibration curve), or any combination thereof. In some examples, the compensation may use a transmitter temperature, and the transmitter temperature may be filtered using Green's function.

In various examples, the method 1100 or 1200 may include determining the humidity of an environment of the sensor based at least in part on a determined impedance. For example, the method may include detection of humidity during transportation of the sensor or during storage of the sensor, or both. In some examples, the performance or operation of a sensor may be affected the humidity environment. In some examples, the method 1100 or method 1200 may include compensating a sensor sensitivity based upon the determined humidity and may optionally include declaring an alert based upon a determined humidity. For example, the method 1100 or 1200 may include delivering an alert using a smart device to alert a user that a sensor should not be used due to excessive humidity exposure.

Each of these non-limiting examples in any portion of the above description may stand on its own or may be combined in various permutations or combinations with one or more of the other examples.

The above detailed description includes references to the accompanying drawings, which form a part of the detailed description. The drawings show, by way of illustration, specific embodiments in which the subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," "third," etc., are used merely as labels, and are not intended to impose numerical requirements on their objects.

Geometric terms, such as "parallel", "perpendicular", "round", or "square" are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the subject matter should be determined with reference to the claims, along with the full scope of equivalents to which such claims are entitled.

What is claimed is:

1. A method comprising:
    disconnecting an analyte sensor from a measurement circuit to begin an accumulation period, wherein the analyte sensor comprises a sensor membrane;
    determining a first impedance characteristic based at least on a measurement during the accumulation period;
    determining a first membrane status based at least on the first impedance characteristic, wherein the first membrane status indicates whether the sensor membrane is damaged;
    reconnecting the analyte sensor to the measurement circuit after the accumulation period;
    receiving a signal from the analyte sensor, wherein the signal is indicative of an amount of charge accumulated on the analyte sensor during the accumulation period;
    determining, after reconnecting the analyte sensor to the measurement circuit, a second impedance characteristic based at least on the signal indicative of the amount of charge accumulated on the analyte sensor during the accumulation period, wherein the second impedance characteristic corresponds to the amount of charge accumulated on the analyte sensor during the accumulation period;
    determining a second membrane status based at least on the second impedance characteristic, wherein the second membrane status indicates whether the sensor membrane is damaged; and
    estimating an analyte concentration dependent at least on both the first membrane status and the second membrane status.

2. The method of claim 1, further comprising:
    using a gate circuit for disconnecting and reconnecting the analyte sensor.

3. The method of claim 1, further comprising:
    determining an estimated analyte concentration level, wherein the estimated analyte concentration level is an estimated glucose concentration level and the amount of charge accumulated relates to an accumulation of hydrogen peroxide during the accumulation period.

4. The method of claim 1, wherein disconnecting and reconnecting of the analyte sensor improves a signal to interference ratio of the analyte sensor.

5. The method of claim 1, further comprising:
    measuring an open cell potential during the accumulation period and determining an open cell potential membrane status based on one or more open cell potentials, wherein the first membrane status includes the open cell potential membrane status.

6. The method of claim 1, wherein the second membrane status includes an interference status.

7. The method of claim 1, wherein at least one of the first membrane status or the second membrane status includes a damage status or a defect status.

8. The method of claim 7, further comprising:
monitoring a current profile after reconnecting the analyte sensor and detecting a membrane fault using the current profile.

9. The method of claim 7, further comprising:
detecting a membrane fault responsive to the second impedance characteristic satisfying a condition.

10. The method of claim 9, wherein the second impedance characteristic is an estimated membrane impedance, a first derivative of impedance, a second derivative impedance, or a fitted curve.

11. The method of claim 9, further comprising: compensating a sensor sensitivity using at least one of the determined first impedance characteristic or the second impedance characteristic.

12. The method of claim 11, wherein:
the first impedance characteristic or the second impedance characteristic is determined using a signal at a frequency that avoids an effect of a double-layer membrane capacitance on the impedance.

13. The method of claim 11, wherein compensating the sensor sensitivity is based on the first impedance characteristic or the second impedance characteristic, and one or more additional factors.

14. The method of claim 13, wherein the one or more additional factors include temperature, a calibration curve, or both.

15. The method of claim 14, wherein the compensation uses a transmitter temperature, and the transmitter temperature is filtered using Green's function.

16. The method of claim 9, wherein the determined second impedance characteristic is used to determine humidity of an environment of the analyte sensor.

17. The method of claim 16, further comprising: compensating a sensor sensitivity based upon the determined humidity.

18. The method of claim 16, further comprising: declaring an alert based upon a determined humidity.

19. The method of claim 18, wherein the alert is declared using a smart device to alert a user that the analyte sensor should not be used due to excessive humidity exposure.

20. The method of claim 1, wherein estimating the analyte concentration comprises compensating for sensor membrane damage based at least on the first membrane status and the second membrane status.

21. The method of claim 1, wherein estimating the analyte concentration comprises compensating for sensor membrane damage based on at least one of the first membrane status or the second membrane status.

22. The method of claim 1, further comprising assessing an integrity of the sensor membrane based on both the first membrane status and the second membrane status.

23. A continuous analyte sensor comprising:
an analyte sensor comprising a sensor membrane; and
sensor electronics operatively coupled to the analyte sensor to receive a signal indicative of an analyte concentration from the analyte sensor, the sensor electronics comprising a measurement circuit, wherein the sensor electronics disconnects the measurement circuit from the analyte sensor and reconnects the analyte sensor to the measurement circuit after an accumulation period, wherein the measurement circuit measures an accumulated charge from the analyte sensor after reconnection of the analyte sensor to the measurement circuit, and wherein the sensor electronics:
determine a first impedance characteristic based at least on a measurement during the accumulation period;
determine a first membrane status based at least on the first impedance characteristic, wherein the first membrane status indicates whether the sensor membrane is damaged;
determine a second impedance characteristic based at least on an analyte signal indicative of the accumulated charge;
determine a second membrane status based at least on the second impedance characteristic, wherein the second membrane status indicates whether the sensor membrane is damaged; and
compensate for damage of the sensor membrane based at least on the first membrane status and the second membrane status.

24. The continuous analyte sensor of claim 23, wherein the sensor electronics determine an estimated analyte concentration level based on the measurement of the accumulated charge.

25. The continuous analyte sensor of claim 23, wherein the sensor electronics comprise a gate circuit for disconnecting and reconnecting the analyte sensor from the measurement circuit.

26. The continuous analyte sensor of claim 23, wherein the analyte concentration is a glucose concentration and an amount of accumulated charge relates to an accumulation of hydrogen peroxide during the accumulation period.

27. The continuous analyte sensor of claim 23, wherein disconnecting and reconnecting of the analyte sensor improves a signal to interference ratio of the analyte sensor.

28. The continuous analyte sensor of claim 23, wherein the sensor electronics measure an open cell potential during a period of time that the analyte sensor is disconnected and determine an open cell potential membrane status based on a profile of the open cell potential, wherein the first membrane status includes the open cell potential membrane status.

29. The continuous analyte sensor of claim 23, wherein the second membrane status includes an interference status.

30. The continuous analyte sensor of claim 23, wherein the second membrane status includes a damage status or a defect status.

31. The continuous analyte sensor of claim 30, wherein the sensor electronics:
monitor a current profile of the analyte signal received from the analyte sensor after reconnection of the analyte sensor; and
detect a membrane fault using the current profile.

32. The continuous analyte sensor of claim 30, wherein the sensor electronics detect a membrane fault responsive to the second impedance characteristic satisfying a condition.

* * * * *